(12) United States Patent
Kim et al.

(10) Patent No.: US 9,012,042 B2
(45) Date of Patent: Apr. 21, 2015

(54) CONDENSED-CYCLIC COMPOUND, ORGANIC LIGHT-EMITTING DEVICE COMPRISING THE SAME, AND FLAT PANEL DISPLAY APPARATUS

(75) Inventors: Hee-Yeon Kim, Yongin (KR); Seung-Gak Yang, Yongin (KR); Jeoung-In Yi, Yongin (KR); Jae-Yong Lee, Yongin (KR)

(73) Assignee: Samsung Display Co., Ltd., Giheung-Gu, Yongin, Gyeonggi-Do (KR)

( * ) Notice: Subject to any disclaimer, the term of this patent is extended or adjusted under 35 U.S.C. 154(b) by 693 days.

(21) Appl. No.: 13/243,817

(22) Filed: Sep. 23, 2011

(65) Prior Publication Data

US 2012/0286246 A1 Nov. 15, 2012

(30) Foreign Application Priority Data

May 13, 2011 (KR) .................... 10-2011-0045117

(51) Int. Cl.
| | |
|---|---|
| *H01L 51/54* | (2006.01) |
| *C07D 487/04* | (2006.01) |
| *C07D 471/04* | (2006.01) |
| *H01L 51/00* | (2006.01) |
| *H01L 51/50* | (2006.01) |

(52) U.S. Cl.
CPC ............ *C07D 471/04* (2013.01); *C07D 487/04* (2013.01); *H01L 51/0055* (2013.01); CPC . *H01L51/0065* (2013.01); *H01L 51/0067* (2013.01); *H01L 51/5056* (2013.01); *Y10S 428/917* (2013.01)

(58) Field of Classification Search
CPC ............... C07D 471/04; C07D 487/04; H01L 51/0055; H01L 51/0065; H01L 51/0067; H01L 51/5056
See application file for complete search history.

(56) References Cited

U.S. PATENT DOCUMENTS

| 5,645,948 A | 7/1997 | Shi et al. |
| 6,559,256 B2 | 5/2003 | Holmes et al. |

(Continued)

FOREIGN PATENT DOCUMENTS

| JP | 11-345686 | 12/1999 |
| KR | 10-0852118 | 8/2008 |
| KR | 10-2009-0118859 | 11/2009 |
| KR | 10-2010-0027950 | 3/2010 |
| WO | WO 2010/150988 | * 12/2010 |

OTHER PUBLICATIONS

Translation for WO 2010/150988 (publication date Dec. 2010).*

*Primary Examiner* — Dawn L. Garrett
(74) *Attorney, Agent, or Firm* — Robert E. Bushnell, Esq.

(57) ABSTRACT

A condensed-cyclic compound represented by Formula 1 below, an organic light-emitting device including the same, and a flat panel display apparatus including the organic light-emitting device:

<Formula 1>

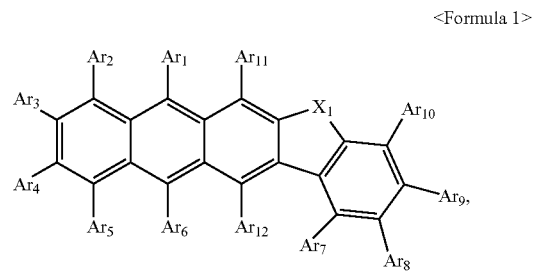

$X_1$, $Ar_1$, $Ar_2$, $Ar_3$, $Ar_4$, $Ar_5$, $Ar_6$, $Ar_7$, $Ar_8$, $Ar_9$, $Ar_{10}$, $Ar_{11}$, and $Ar_{12}$ being described in the detailed description of the invention. The organic light-emitting device including an organic layer including the compound above has low driving voltage and high emission efficiency.

16 Claims, 2 Drawing Sheets

(56) References Cited

U.S. PATENT DOCUMENTS

| | | |
|---|---|---|
| 2006/0154105 A1* | 7/2006 | Yamamoto et al. ............ 428/690 |
| 2008/0224129 A1* | 9/2008 | Choi et al. ...................... 257/40 |
| 2008/0226945 A1 | 9/2008 | Kim et al. |
| 2011/0057182 A1 | 3/2011 | Lee et al. |
| 2012/0181520 A1* | 7/2012 | Kim et al. ....................... 257/40 |
| 2012/0187392 A1* | 7/2012 | Ito et al. ......................... 257/40 |
| 2012/0286249 A1* | 11/2012 | Lee et al. ....................... 257/40 |
| 2013/0207048 A1* | 8/2013 | Schwaiger et al. ........... 252/500 |

* cited by examiner

CONDENSED-CYCLIC COMPOUND, ORGANIC LIGHT-EMITTING DEVICE COMPRISING THE SAME, AND FLAT PANEL DISPLAY APPARATUS

CLAIM OF PRIORITY

This application claims the benefit of Korean Patent Application No. 10-2011-0045117, filed on May 13, 2011, in the Korean Intellectual Property Office, the disclosure of which is incorporated herein in its entirety by reference.

BACKGROUND OF THE INVENTION

1. Field of the Invention

The present invention relates to a condensed-cyclic compound, an organic light-emitting device including the same, and a flat panel display apparatus including the organic light-emitting device, and more particularly, to a condensed-cyclic compound which is suitable to be used in an electron transport layer of an organic light-emitting device, the organic light-emitting device including the condensed-cyclic compound, and a flat panel display apparatus including the organic light-emitting device. The organic light-emitting device that includes an organic layer including the condensed-cyclic compound has characteristics of low driving voltage and high light-emitting efficiency.

2. Description of the Related Art

Organic light-emitting devices are self light-emitting devices which have wide viewing angles, excellent contrast, rapid response times, excellent brightness, driving voltage, and response speeds, and are multicolored.

In a general organic light-emitting device, an anode is formed on a substrate, and a hole transport layer, an emission layer, an electron transport layer, and a cathode are sequentially formed on the anode. Here, the hole transport layer, the emission layer, and the electron transport layer are organic thin film layers including an organic compound.

A driving principle of the organic light-emitting device is as follows. When voltage is applied between the anode and the cathode, holes injected from the anode move to the emission layer through the hole transport layer, and electrons injected from the cathode move to the emission layer through the electron transport layer. Carriers such as the holes and the electrons are recombined at the emission layer and produce excitons. Such excitons are changed from an excitation state to a ground state, thereby generating light.

A general organic light-emitting device still needs to be improved in terms of driving voltage, light-emitting efficiency, and lifetime.

SUMMARY OF THE INVENTION

The present invention provides a condensed-cyclic compound, an organic light-emitting device including the condensed-cyclic compound, and a flat panel display apparatus including the organic light-emitting device.

According to an aspect of the present invention, there is provided a condensed-cyclic compound represented by Formula 1 below:

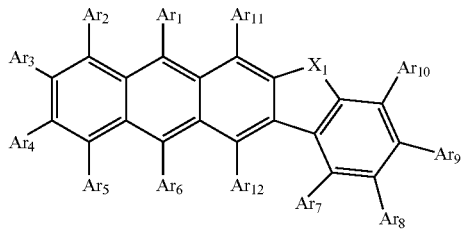

<Formula 1> wherein $X_1$ is $CR_1R_2$, $NR_3$, or O;

$Ar_1$ through $Ar_{12}$ are each independently one selected from the group consisting of a hydrogen atom, deuterium, a halogen atom, a hydroxyl group, a cyano group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ aryloxy group, a substituted or unsubstituted $C_5$-$C_{30}$ arylthio group, a substituted or unsubstituted $C_2$-$C_{30}$ heterocyclic group, a group represented by Formula 2 below, a group represented by $N(Q_1)(Q_2)$, and a group represented by $Si(Q_3)(Q_4)(Q_5)$, wherein $Q_1$ through $Q_5$ are each independently one selected from the group consisting of a hydrogen atom, deuterium, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ aryloxy group, a substituted or unsubstituted $C_5$-$C_{30}$ arylthio group, and a substituted or unsubstituted $C_2$-$C_{30}$ heterocyclic group, at least one of $Ar_1$ through $Ar_{12}$ is a group represented by Formula 2 below;

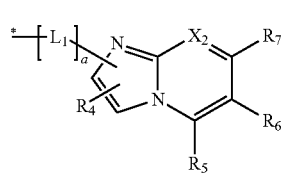

<Formula 2>

$L_1$ is a substituted or unsubstituted $C_1$-$C_{30}$ alkylene group, a substituted or unsubstituted $C_5$-$C_{30}$ arylene group, or a substituted or unsubstituted divalent $C_2$-$C_{30}$ heterocyclic group;

$X_2$ is $CR_8$ or N;

a is an integer from 0 to 5; and $R_1$ through $R_8$ are each independently one selected from the group consisting of a hydrogen atom, deuterium, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ aryloxy group, a substituted or unsubstituted $C_5$-$C_{30}$ arylthio group, and a substituted or unsubstituted $C_2$-$C_{30}$ heterocyclic group, wherein at least two of $R_4$ through $R_8$ that are adjacent to each other may be combined with each other to form a saturated or unsaturated ring and plural groups in $R_4$ through $R_8$ may be the same as each other or different from each other.

According to another aspect of the present invention, there is provided an organic light-emitting device including: a first electrode; a second electrode facing the first electrode; and an organic light-emitting device comprising at least one organic layer interposed between the first electrode and the second electrode, wherein the at least one organic layer comprises the condensed-cyclic compound represented by Formula 1 above.

According to another aspect of the present invention, there is provided a flat panel display apparatus comprising a transistor comprising a source electrode, a drain electrode, a gate, and an active layer, and the organic light-emitting device above, wherein a first electrode of the organic light-emitting device is electrically connected to the source electrode or the drain electrode.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
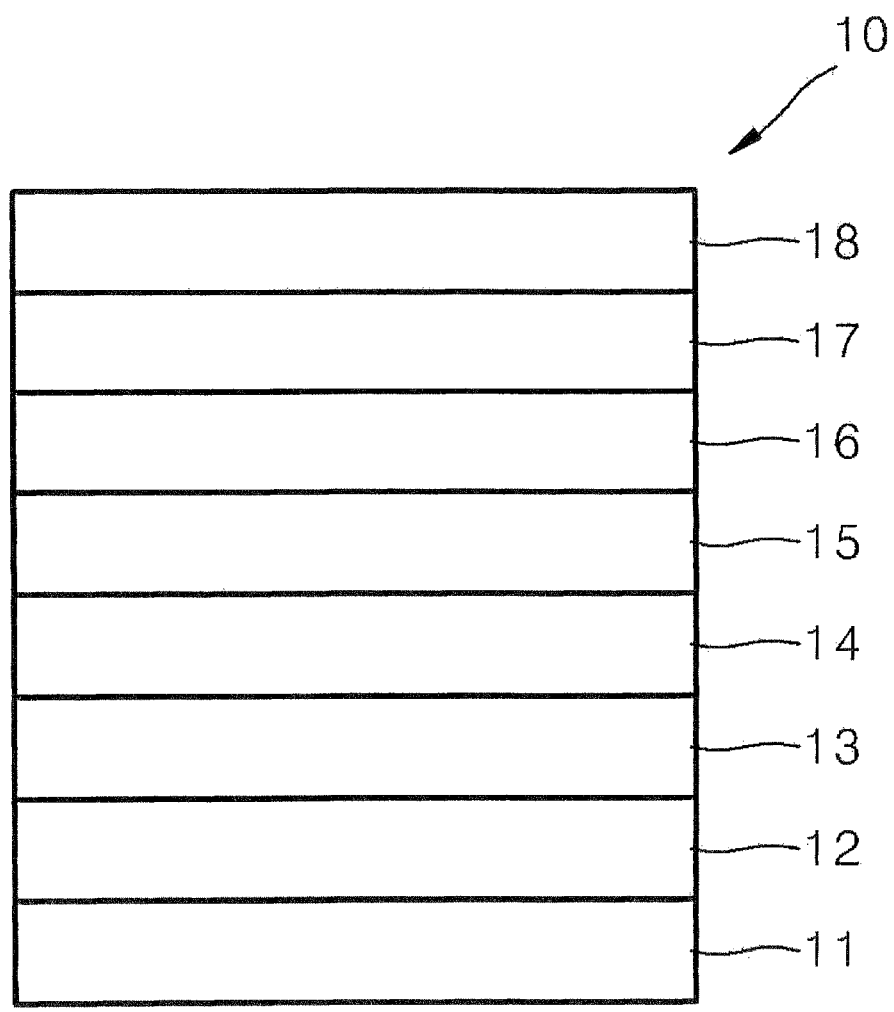
FIG. 1 is a cross-sectional view of an organic light-emitting device according to an embodiment of the present invention.
Figure 2:
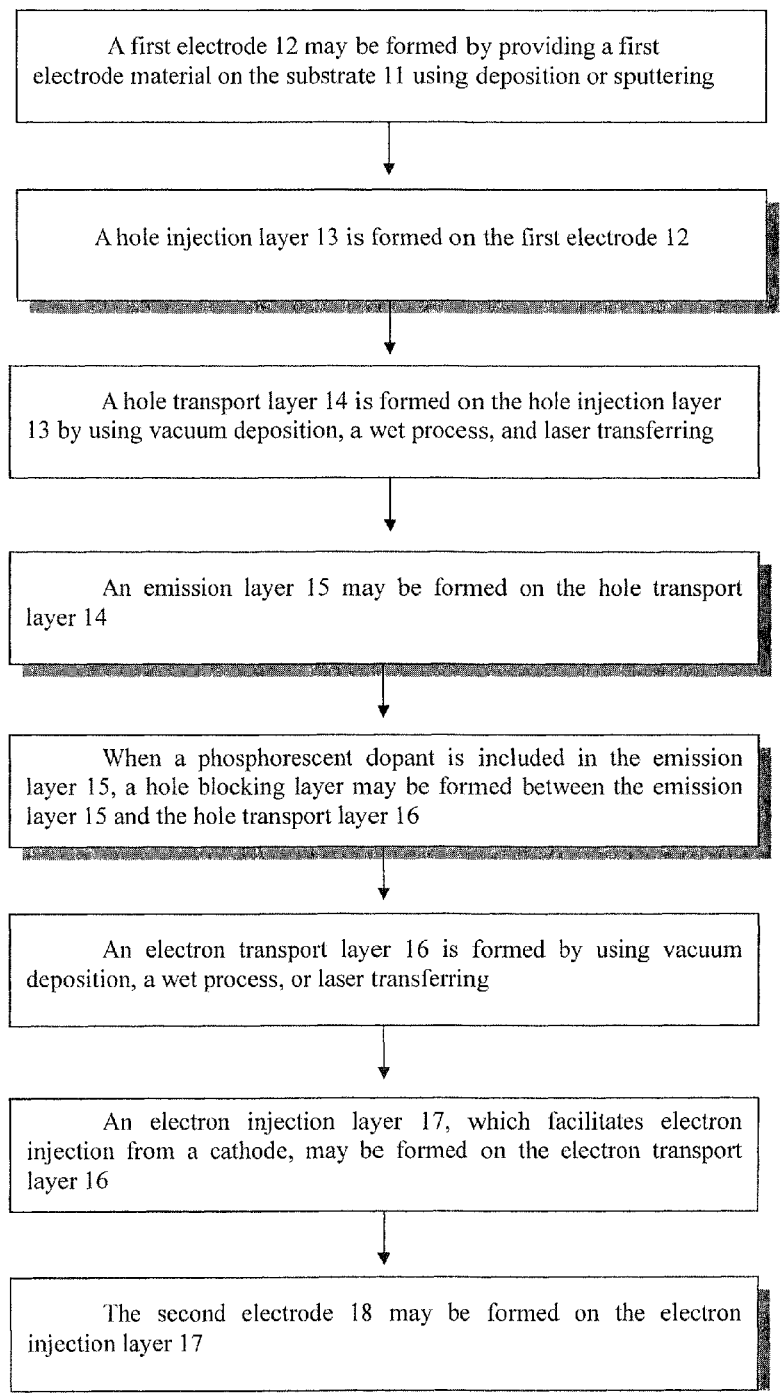
FIG. 2 is a flow chart showing a method of making an organic light emitting device according to an embodiment of the present invention.

A condensed-cyclic compound represented by Formula 1 below is provided according to an embodiment of the present invention:

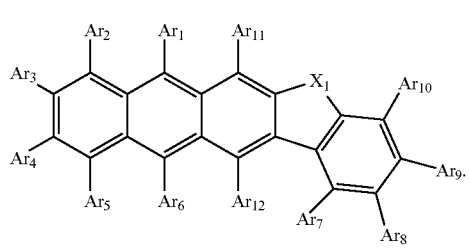

<Formula 1> wherein $X_1$ is $CR_1R_2$, $NR_3$, or O;

$Ar_1$ through $Ar_{12}$ are each independently one selected from the group consisting of a hydrogen atom, deuterium, a halogen atom, a hydroxyl group, a cyano group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ aryloxy group, a substituted or unsubstituted $C_5$-$C_{30}$ arylthio group, a substituted or unsubstituted $C_2$-$C_{30}$ heterocyclic group, a group represented by Formula 2 below, a group represented by $N(Q_1)(Q_2)$, and a group represented by $Si(Q_3)(Q_4)(Q_5)$, wherein at least one of $Ar_1$ through $Ar_{12}$ is a group represented by Formula 2 below;

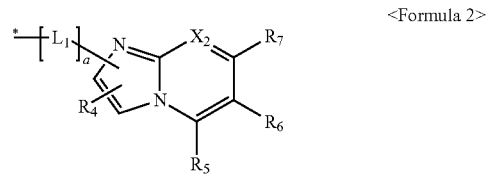

<Formula 2>

$L_1$ is a substituted or unsubstituted $C_1$-$C_{30}$ alkylene group, a substituted or unsubstituted $C_5$-$C_{30}$ arylene group, or a substituted or unsubstituted divalent $C_2$-$C_{30}$ heterocyclic group;

$X_2$ is $CR_8$ or N;

a is an integer from 0 to 5; and $R_1$ through $R_8$ are each independently one selected from the group consisting of a hydrogen atom, deuterium, a halogen atom, a hydroxyl group, a cyano group, an amino group, a nitro group, a carboxyl group, a substituted or unsubstituted $C_1$-$C_{30}$alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ aryloxy group, a substituted or unsubstituted $C_5$-$C_{30}$ arylthio group, and a substituted or unsubstituted $C_2$-$C_{30}$ heterocyclic group, wherein at least two of $R_4$ through $R_8$ that are adjacent to each other may be combined with each other to form a saturated or unsaturated ring and plural groups in $R_4$ through $R_8$ may be the same as each other or different from each other.

Here, $Q_1$ through $Q_5$ are each independently one selected from the group consisting of a hydrogen atom, deuterium, a halogen atom, a hydroxyl group, a cyano group, an amino group, a nitro group, a carboxyl group, a substituted or unsubstituted $C_1$-$C_{30}$alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ aryloxy group, a substituted or unsubstituted $C_5$-$C_{30}$ arylthio group, and a substituted or unsubstituted $C_2$-$C_{30}$ heterocyclic group. For example, $Q_1$ through $Q_5$ may be each independently one selected from the group consisting of a hydrogen atom, deuterium, a halogen atom, a hydroxyl group, a cyano group, an amino group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted pentalenyl group, a substituted or unsubstituted indenyl group, a substituted or unsubstituted naphtyl group, a substituted or unsubstituted azulenyl group, a substituted or unsubstituted heptalenyl group, a substituted or unsubstituted indacenyl group, a substituted or unsubstituted acenaphtyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzooxazolyl group, a substituted or unsubstituted benzoimidazolyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted thiazolyl group, a substituted or unsubstituted isothiazolyl group, a substituted or unsubstituted benzothiazolyl group, a substituted or unsubstituted isoxazolyl group, a substituted or unsubstituted oxazolyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted benzooxazolyl group, a substituted or unsubstituted dibenzofuranyl group, and a substituted or unsubstituted dibenzothiophenyl group.

The condensed-cyclic compound represented by Formula 1 above includes a core, in which an anthracene moiety having excellent device characteristics, a fluorene moiety having excellent fluorescent characteristic, and a carbazole moiety, or a furane moiety are fused to each other, and an imidazo pyridinyl group or an imidazo pyrimidinyl group having excellent electron transport capability is combined with the core.

According to an embodiment of the present invention, in the condensed-cyclic compound represented by Formula 1, a part for constituting the core by being fused to an anthracene moiety may be a fluorene moiety having excellent fluorescent characteristic. In this case, in the condensed-cyclic compound represented by Formula 1, $X_1$ in Formula 1 may be $CR_1R_2$.

According to an embodiment of the present invention, $R_1$ and $R_3$ may be each independently one selected from the group consisting of a hydrogen atom, deuterium, a halogen atom, a hydroxyl group, a cyano group, an amino group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted pentalenyl group, a substituted or unsubstituted indenyl group, a substituted or unsubstituted naphtyl group, a substituted or unsubstituted azulenyl group, a substituted or unsubstituted heptalenyl group, a substituted or unsubstituted indacenyl group, a substituted or unsubstituted acenaphtyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzooxazolyl group, a substituted or unsubstituted benzoimidazolyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted thiazolyl group, a substituted or unsubstituted isothiazolyl group, a substituted or unsubstituted benzothiazolyl group, a substituted or unsubstituted isoxazolyl group, a substituted or unsubstituted oxazolyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted benzooxazolyl group, a substituted or unsubstituted dibenzofuranyl group, and a substituted or unsubstituted dibenzothiophenyl group. For example, $R_1$ and $R_3$ may be each independently one selected from the group consisting of a hydrogen atom, deuterium, a halogen atom, a hydroxyl group, a cyano group, an amino group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted naphtyl group, a substituted or unsubstituted fluorenyl group, a substituted or unsubstituted spiro-fluorenyl group, a substituted or unsubstituted anthryl group, a substituted or unsubstituted pyrazolyl group, a substituted or unsubstituted pyridinyl group, a substituted or unsubstituted pyrazinyl group, a substituted or unsubstituted pyrimidinyl group, and a substituted or unsubstituted pyridazinyl group.

According to an embodiment of the present invention, in the condensed-cyclic compound represented by Formula 1, at least one of $Ar_1$ through $Ar_{10}$ in Formula 1 may be a group represented by Formula 2 above, and more specifically, at least one selected from the group consisting of $Ar_1$, $Ar_3$, and $Ar_9$ may be a group represented by Formula 2 above. For example, any one or any two of the group consisting of $Ar_1$, $Ar_3$, and $Ar_9$ may be a group represented by Formula 2 above.

According to an embodiment of the present invention, $Ar_2$, $Ar_5$, $Ar_7$, $Ar_8$, $Ar_{10}$, $Ar_{11}$, and $Ar_{12}$ may be all hydrogen atom, and $Ar_1$, $Ar_3$, $Ar_4$, $Ar_6$, and $Ar_9$ may be each independently one selected from the group consisting of deuterium, a halogen atom, a hydroxyl group, a cyano group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ aryloxy group, a substituted or unsubstituted $C_5$-$C_{30}$ arylthio group, a substituted or unsubstituted $C_2$-$C_{30}$ heterocyclic group, a group represented by Formula 2 above, a group represented by $N(Q_1)(Q_2)$, and a group represented by $Si(Q_3)(Q_4)(Q_5)$. In this case, at least one selected from the group consisting of $Ar_1$, $Ar_3$, and $Ar_9$ may be a group represented by Formula 2 above.

According to an embodiment of the present invention, in Formula 1 above, $Ar_1$ through $Ar_{12}$ are each independently one selected from the group consisting of a hydrogen atom, deuterium, a halogen atom, a hydroxyl group, a cyano group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted pentalenyl group, a substituted or unsubstituted indenyl group, a substituted or unsubstituted naphtyl group, a substituted or unsubstituted azulenyl group, a substituted or unsubstituted heptalenyl group, a substituted or unsubstituted indacenyl group, a substituted or unsubstituted acenaphtyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzooxazolyl group, a substituted or unsubstituted benzoimidazolyl group, a substituted or unsubstituted furanyl, a substituted or unsubstituted benzofuranyl group, a substituted or unsubstituted thiophenyl group, a substituted or unsubstituted benzothiophenyl group, a substituted or unsubstituted thiazolyl group, a substituted or unsubstituted isothiazolyl group, a substituted or unsubstituted benzothiazolyl group, a substituted or unsubstituted isoxazolyl group, a substituted or unsubstituted oxazolyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted benzooxazolyl group, a substituted or unsubstituted dibenzofuranyl group, a substituted or unsubstituted dibenzothiophenyl group, a group represented by Formula 2 above, a group represented by $N(Q_1)(Q_2)$, and a group represented by $Si(Q_3)(Q_4)(Q_5)$.

According to an embodiment of the present invention, the condensed-cyclic compound represented by Formula 1 above includes a core, in which an anthracene moiety having excellent device characteristics, a fluorene moiety having excellent fluorescent characteristic, and a carbazole moiety, or a furane moiety are fused to each other, and an imidazo pyridinyl group is combined with the core. In this case, at least one of $Ar_1$ through $Ar_{12}$, which is a part other than the core in Formula 1 above, may include an imidazopyridinyl group having excellent electron transport capability, and $X_2$ in Formula 2 above may be $CR_8$. Here, $R_8$ is the same as defined in formula 2 above.

According to an embodiment of the present invention, at least two of $R_4$ through $R_8$ that are adjacent to each other may be combined with each other to form a saturated or unsaturated ring, for example, $R_7$ and $R_8$ may be combined with each other to form a $C_6$ unsaturated ring.

According to an embodiment of the present invention, the condensed-cyclic compound represented by Formula 1 has a structure, in which an imidazopyrimidinyl group is combined to the core. In this case, at least one of $Ar_1$ through $Ar_{12}$, which is a part other than the core in Formula 1 above, may include an imidazopyrimidinyl group having excellent electron transport capability, and $X_2$ in Formula 2 above may be N.

According to an embodiment of the present invention, the condensed-cyclic compound represented by Formula 1 includes Formula 2, and $L_1$ in Formula 2 may be one selected from the group consisting of a substituted or unsubstituted $C_1$-$C_{30}$ alkylene group, a substituted or unsubstituted $C_5$-$C_{30}$ arylene group, and a substituted or unsubstituted divalent $C_2$-$C_{30}$ heterocyclic group, for example, a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphtylene group, a substituted or unsubstituted fluorenylene group, a substituted or unsubstituted spiro-fluorenyl group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenyl group, a substituted or unsubstituted naphthacenyl group, a substituted or unsubstituted picenyl group, a substituted or unsubstituted perylenylene group, a substituted or unsubstituted pentaphenylene group, and a substituted or unsubstituted hexylenylene group.

According to an embodiment of the present invention, a in Formula 2 above may be 1 or 2, for example, 1.

According to an embodiment of the present invention, R₄ through R₈ in Formula 2 above may be each independently one selected from the group consisting of a hydrogen atom, deuterium, a halogen atom, a hydroxyl group, a cyano group, an amino group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted naphtyl group, a substituted or unsubstituted fluorenyl group, a substituted or unsubstituted spiro-fluorenyl group, a substituted or unsubstituted anthryl group, a substituted or unsubstituted pyrazolyl group, a substituted or unsubstituted pyridinyl group, a substituted or unsubstituted pyrazinyl group, a substituted or unsubstituted pyrimidinyl group, and a substituted or unsubstituted pyridazinyl group.

In the condensed-cyclic compound represented by Formula 1, the group represented by Formula 2 above may be a condensed-cyclic compound represented by Formulas 2A through 2N below:

<Formula 2A>
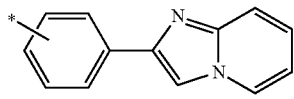

<Formula 2B>
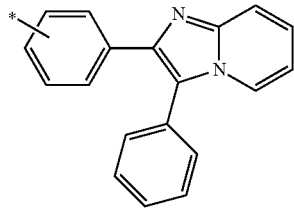

<Formula 2C>
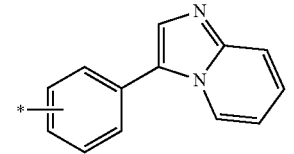

<Formula 2D>
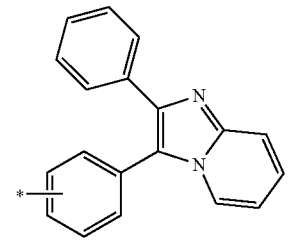

<Formula 2E>
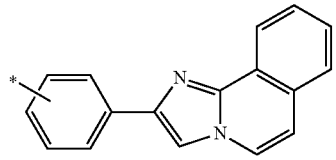

<Formula 2F>
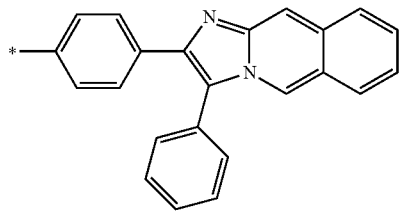

<Formula 2G>
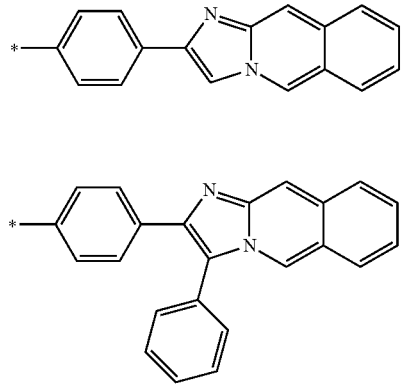

<Formula 2H>
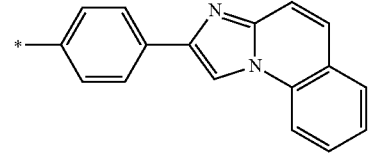

<Formula 2I>
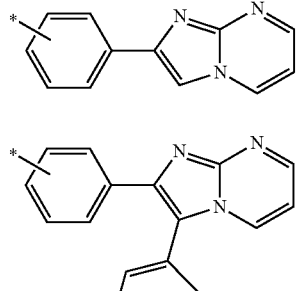

<Formula 2J>
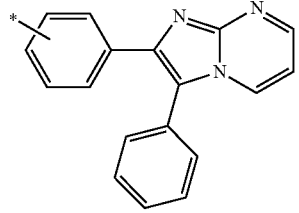

<Formula 2K>
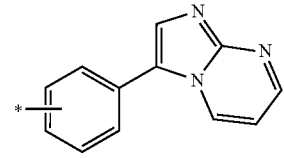

<Formula 2L>
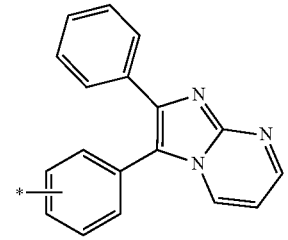

-continued
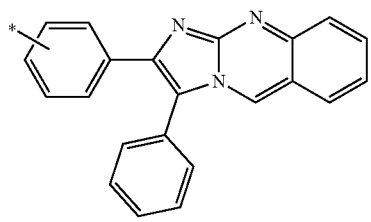
<Formula 2M>
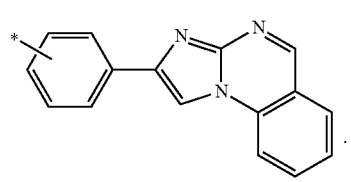
<Formula 2N>
In the above formulas "*" represents a chemical bond.
More specifically, the condensed-cyclic compound represented by Formula 1 may be, but is not limited to, one of compounds represented by Compounds 1 through 103 below:
<Compound 1>
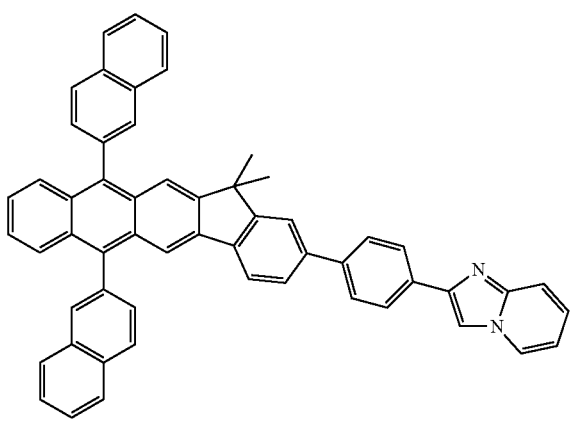
<Compound 2>
-continued
<Compound 3>
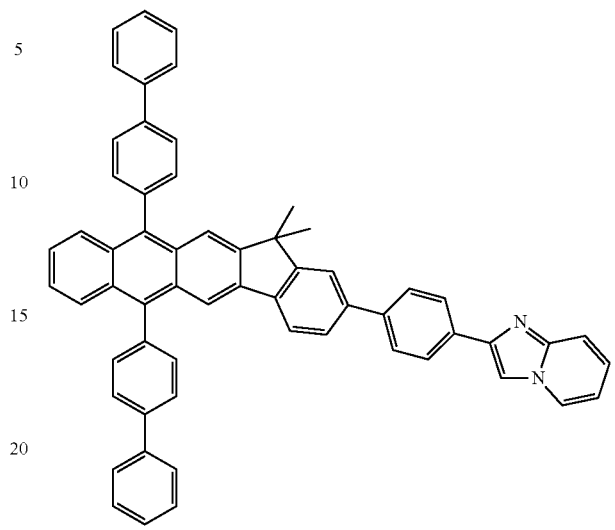
<Compound 4>
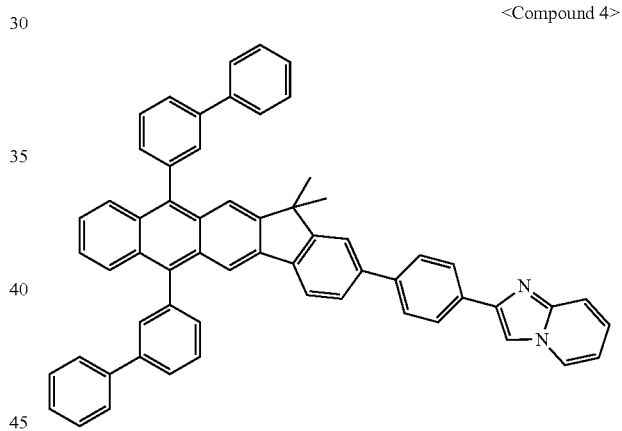
<Compound 5>
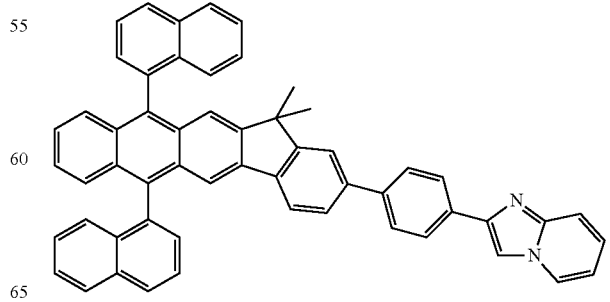

<Compound 6>
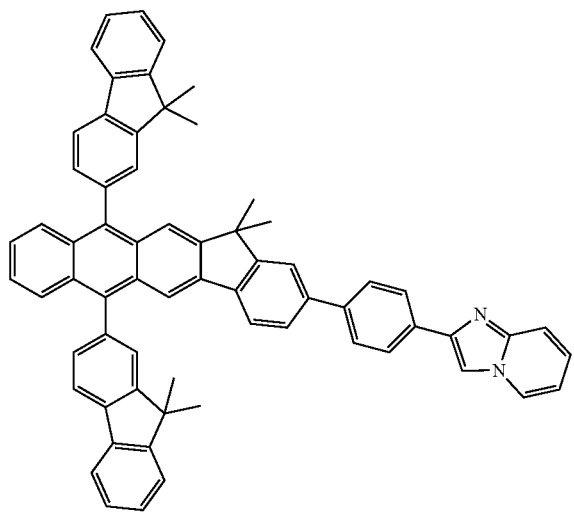
<Compound 7>
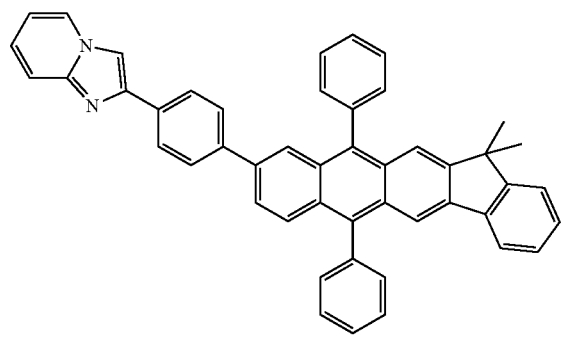
<Compound 8>
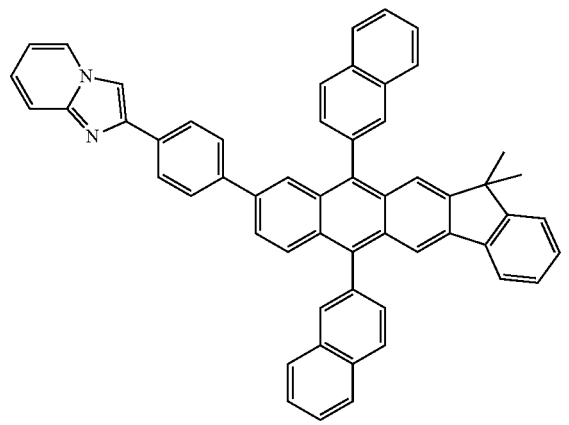
<Compound 9>
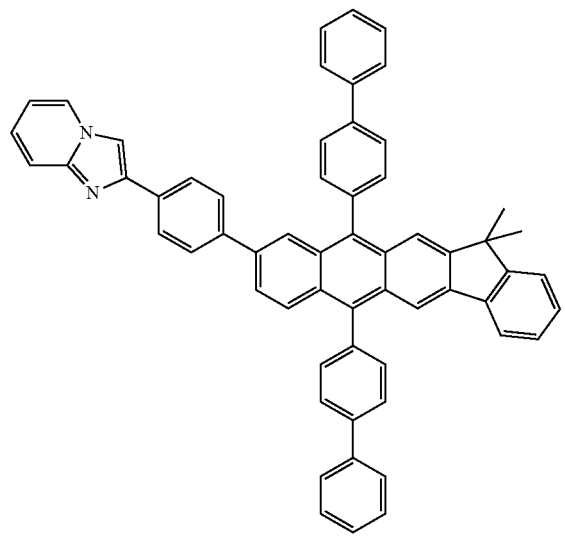
<Compound 10>
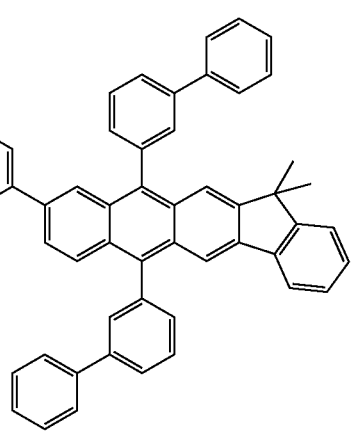
<Compound 11>
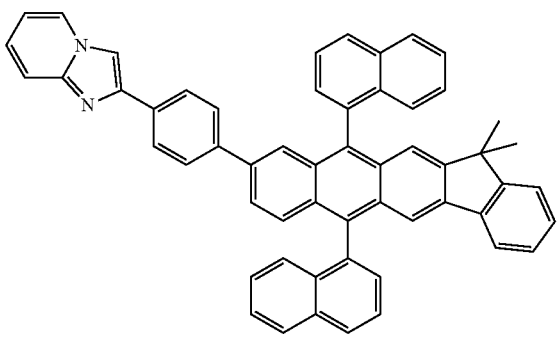

<Compound 12>
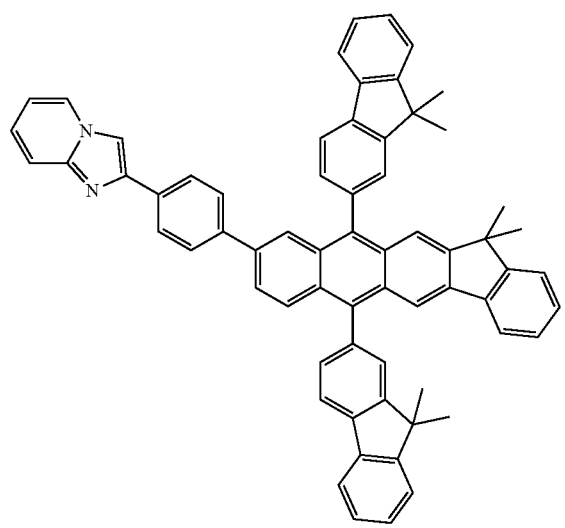
<Compound 13>
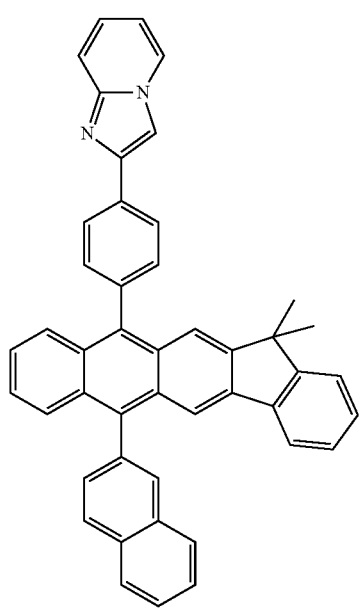
<Compound 14>
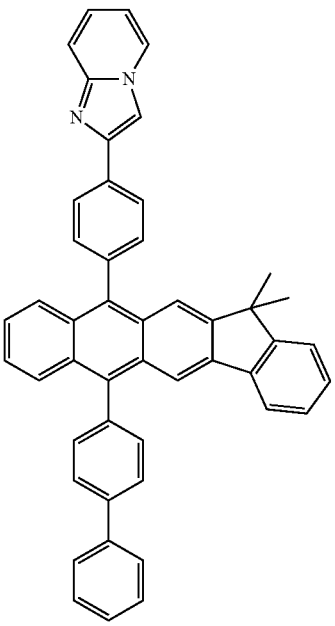
<Compound 15>
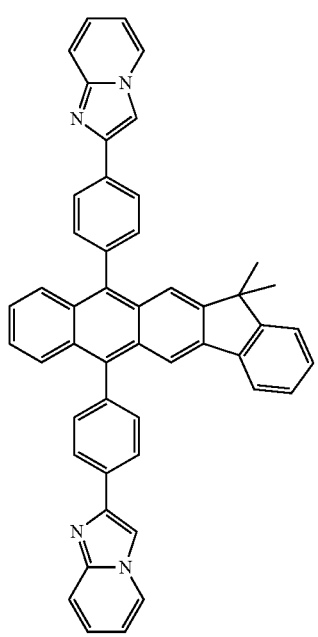

<Compound 16>
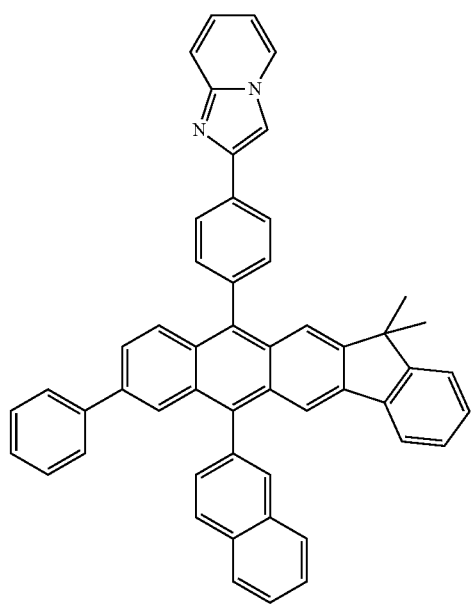
<Compound 18>
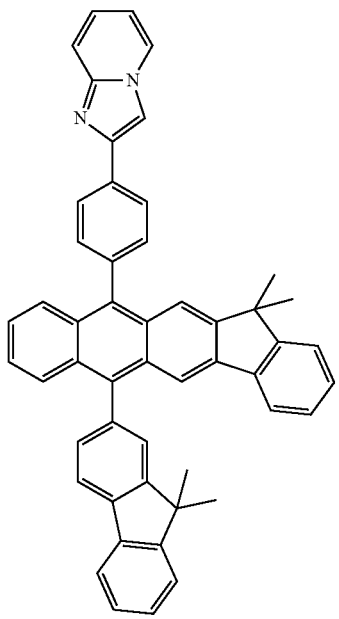
<Compound 17>
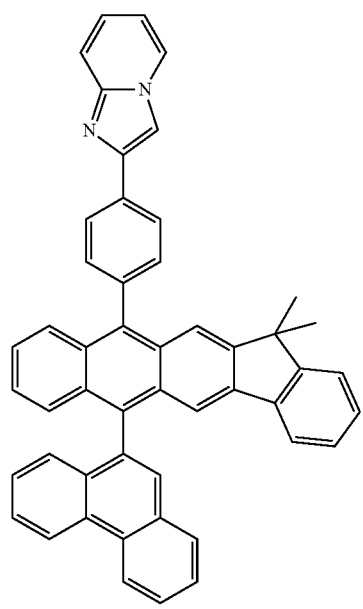
<Compound 19>
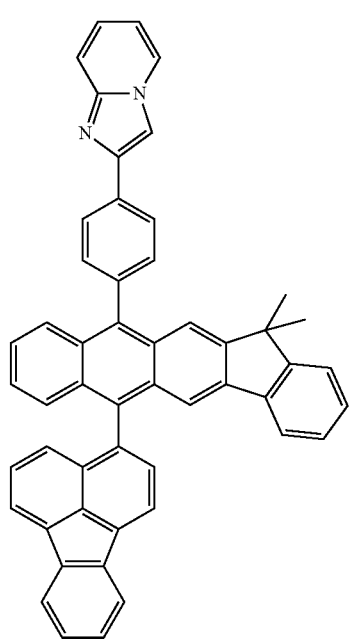

<Compound 20>
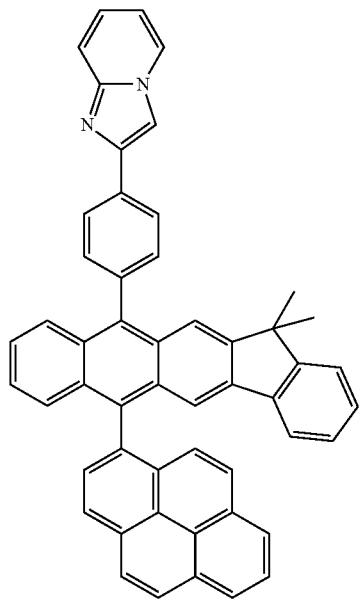
<Compound 23>
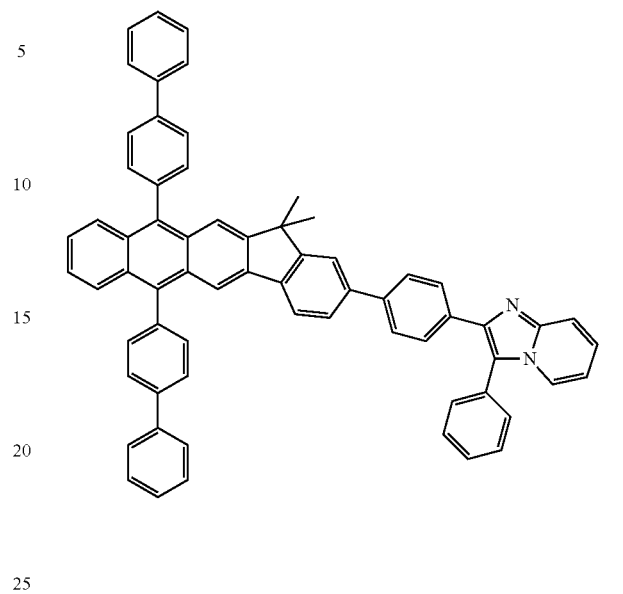
<Compound 21>
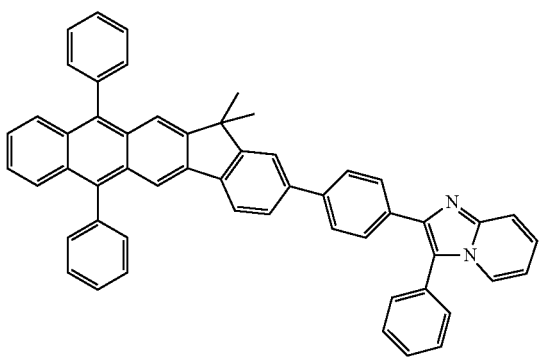
<Compound 24>
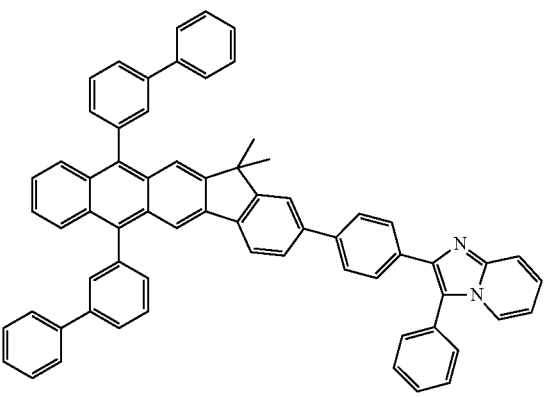
<Compound 22>
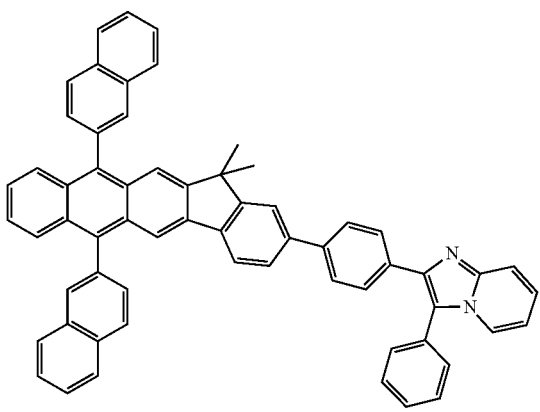
<Compound 25>
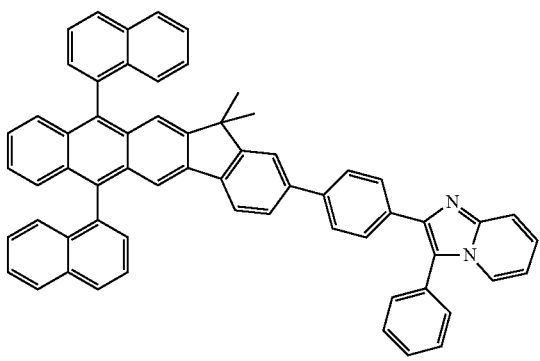

<Compound 26>
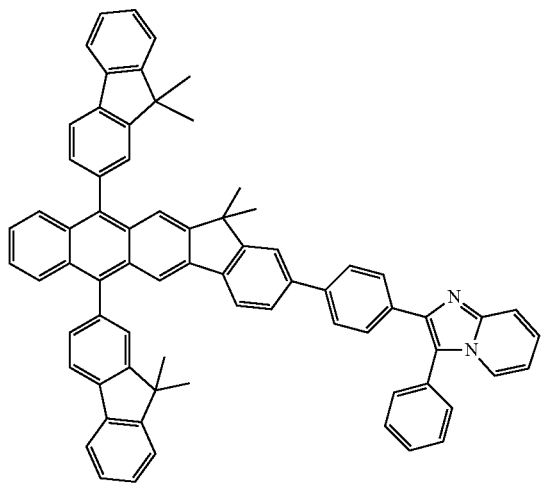
<Compound 27>
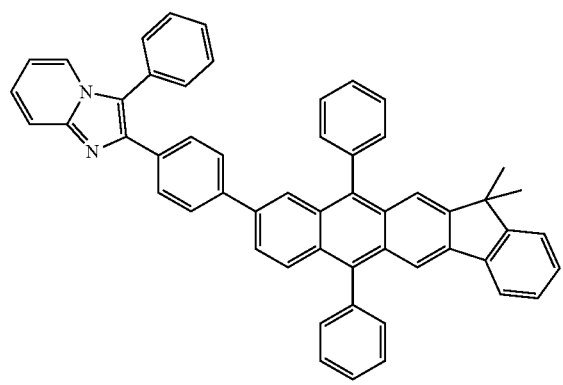
<Compound 28>
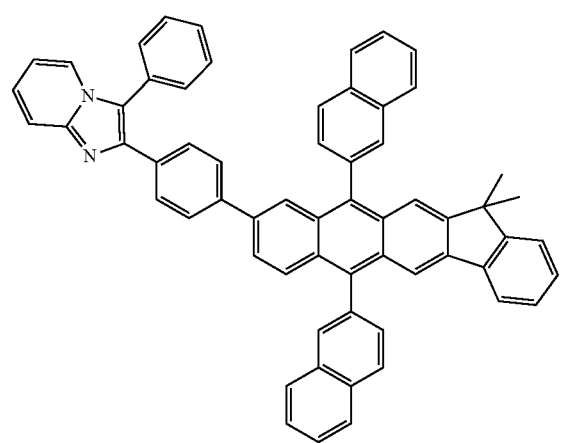
<Compound 29>
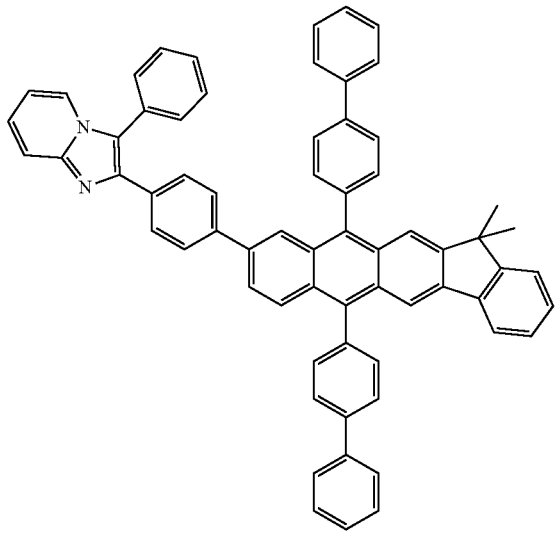
<Compound 30>
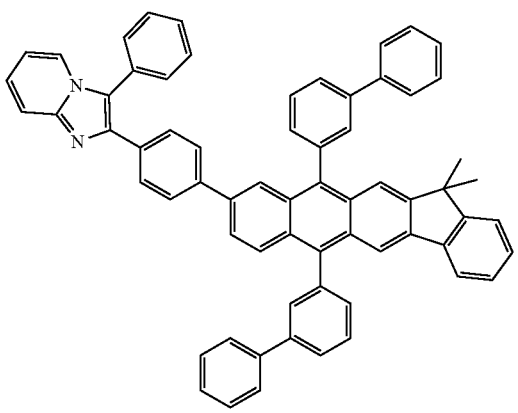
<Compound 31>
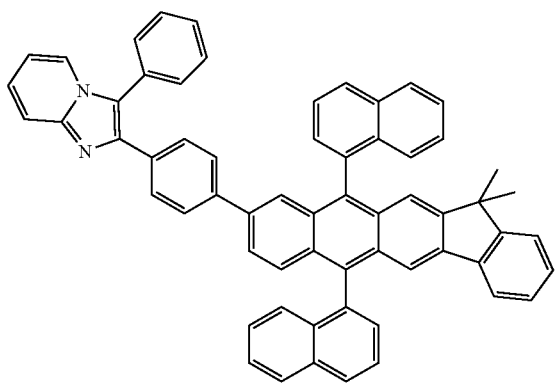

<Compound 32>
<Compound 33>
<Compound 34>
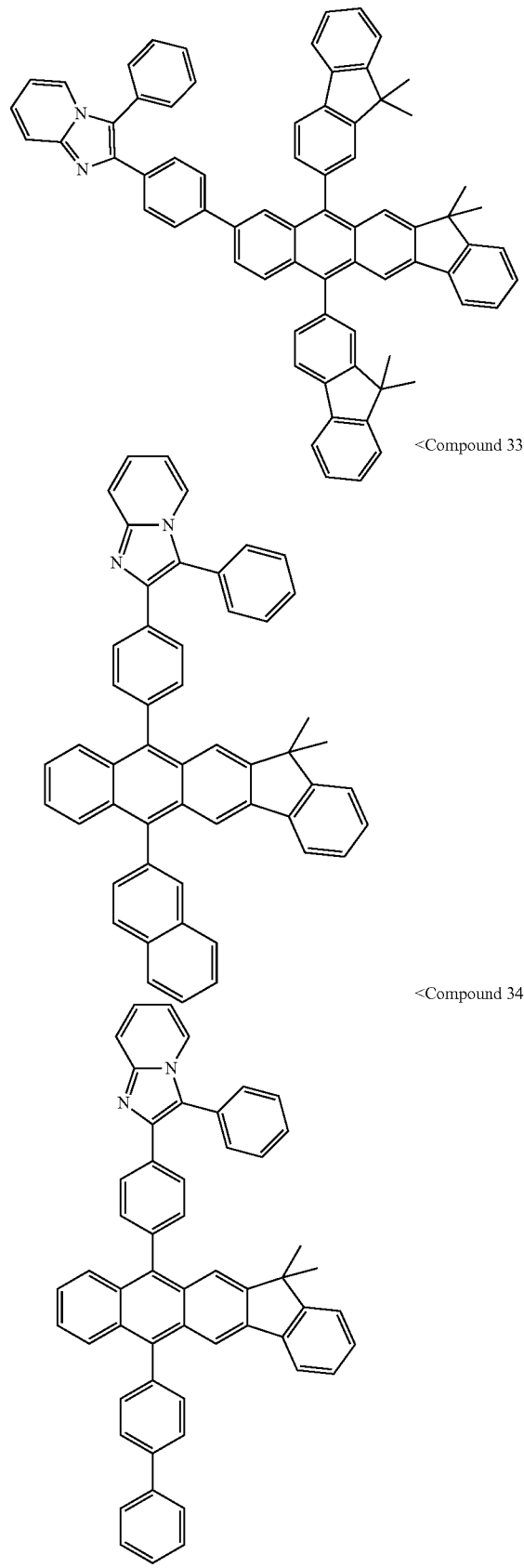
<Compound 35>
<Compound 36>
<Compound 37>
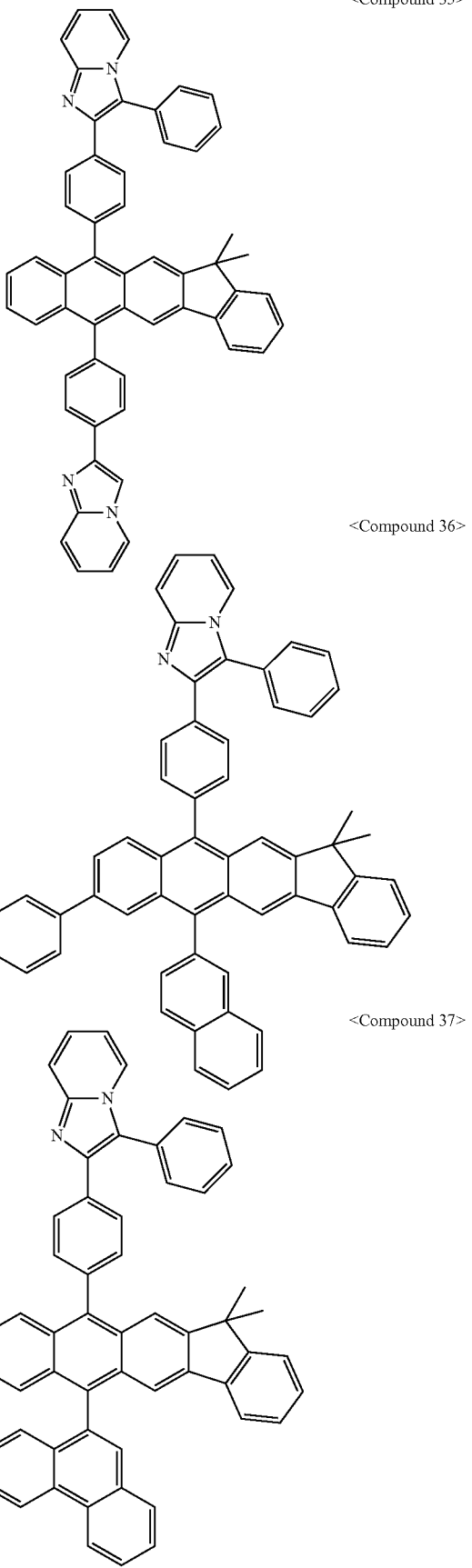

<Compound 38>
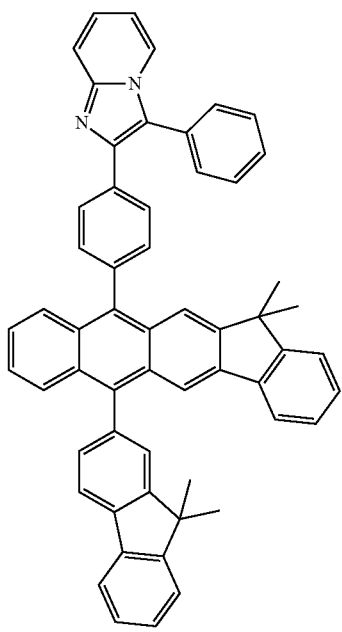
<Compound 40>
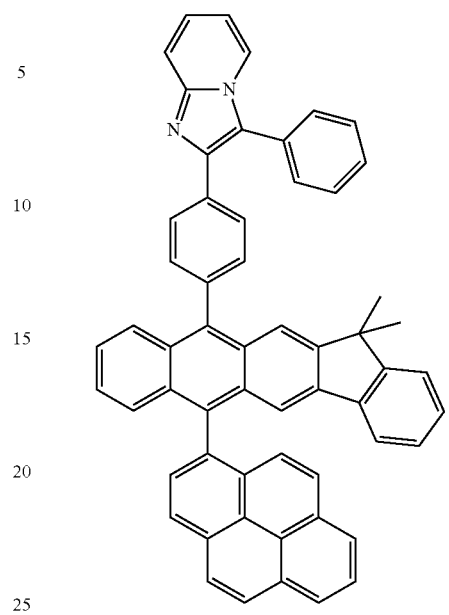
<Compound 41>
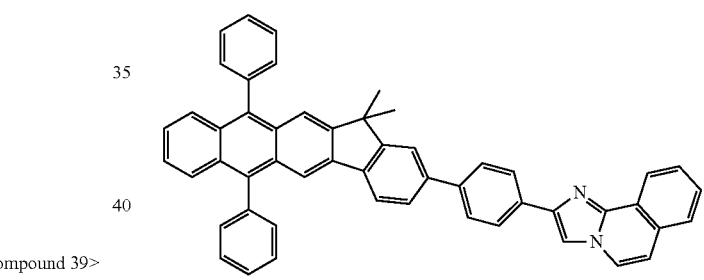
<Compound 39>
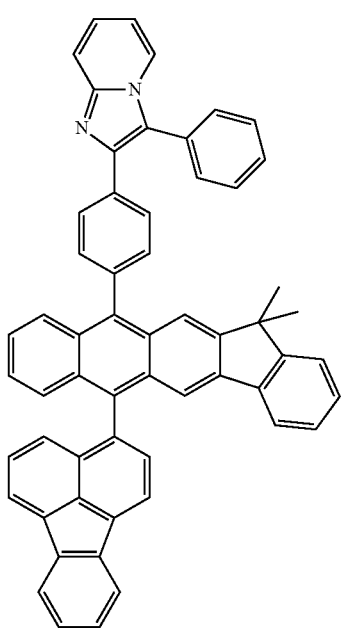
<Compound 42>
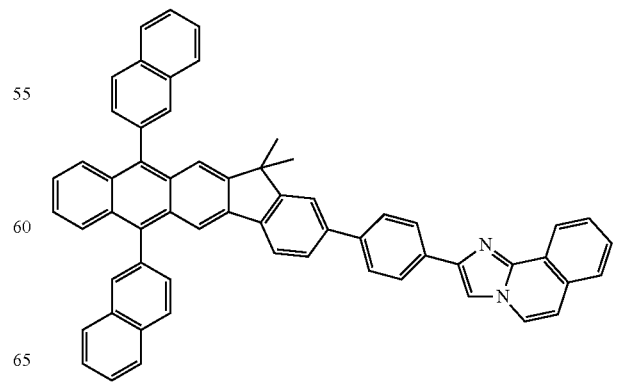

<Compound 43>
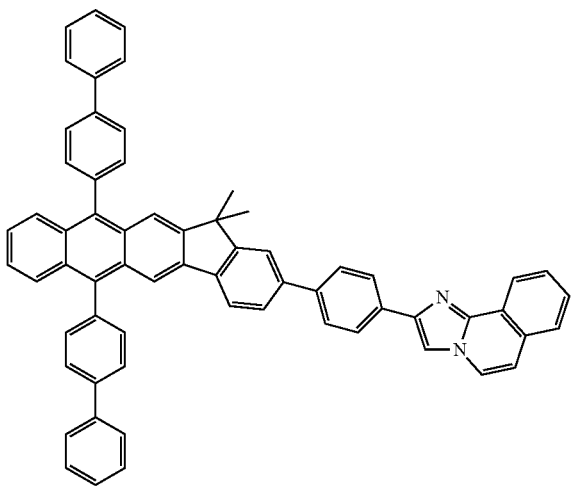
<Compound 46>
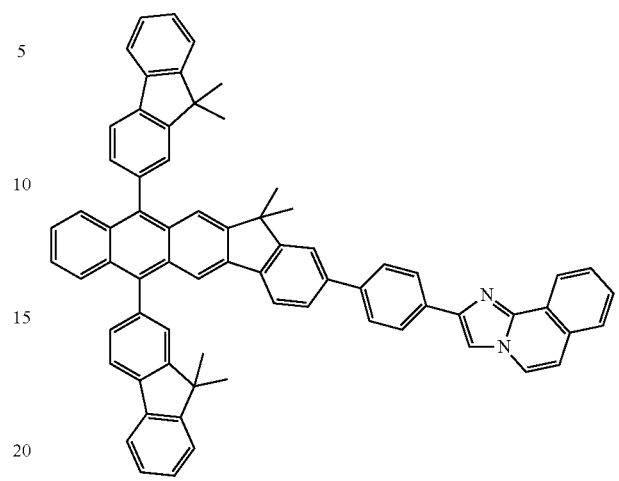
<Compound 44>
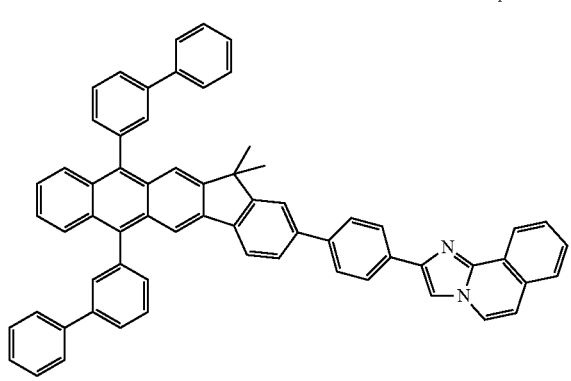
<Compound 47>
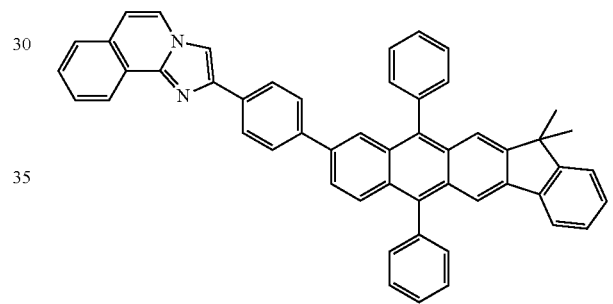
<Compound 45>
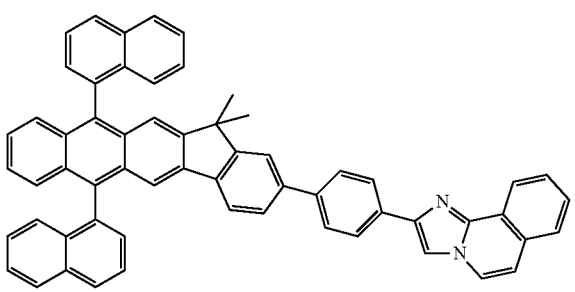
<Compound 48>
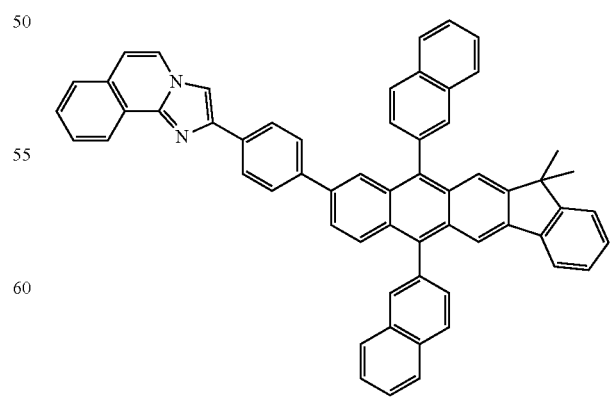

<Compound 49>
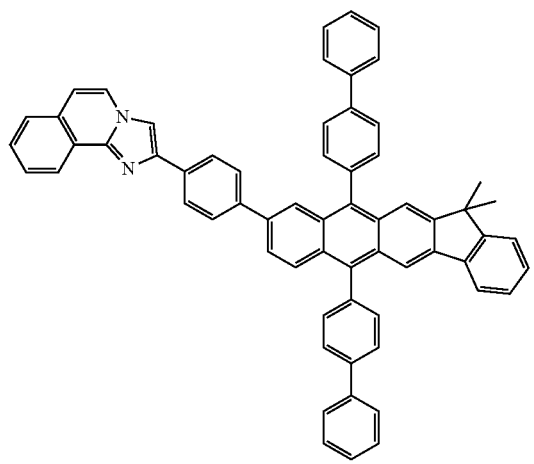
<Compound 50>
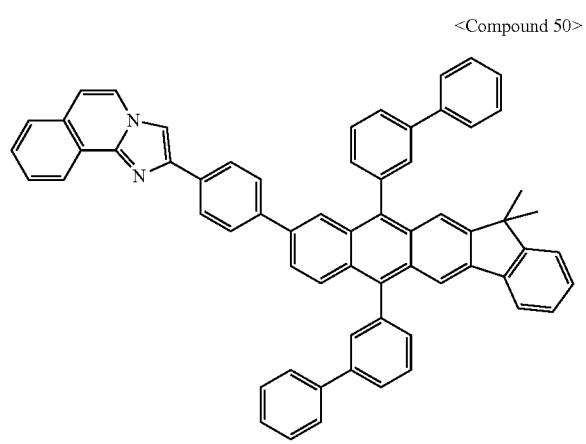
<Compound 51>
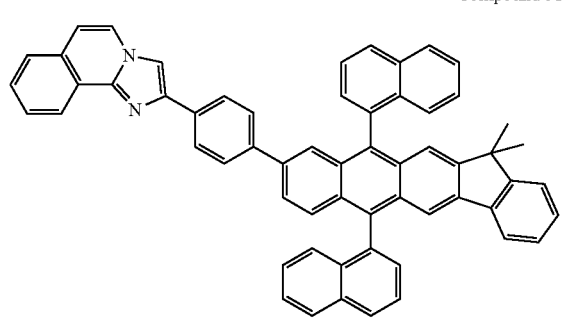
<Compound 52>
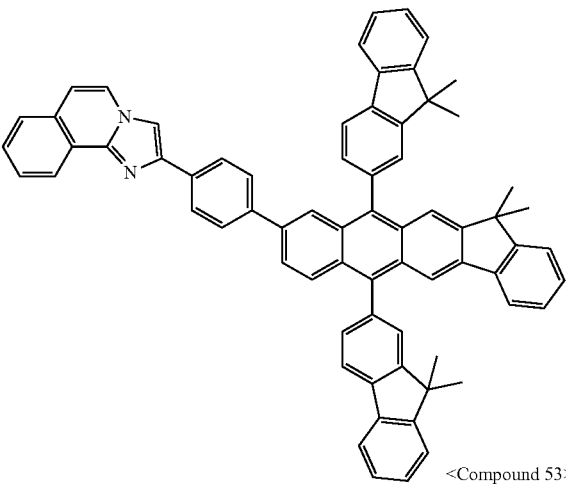
<Compound 53>
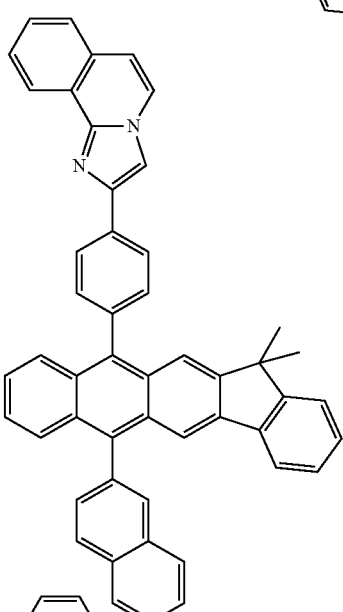
<Compound 54>
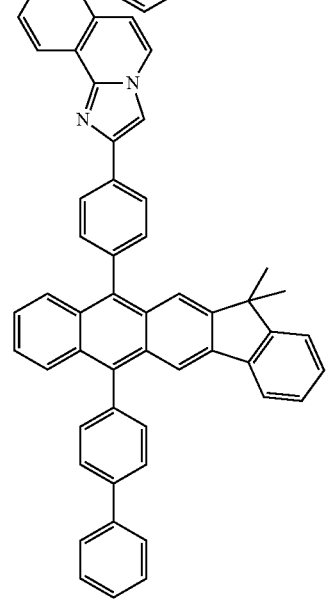

<Compound 55>
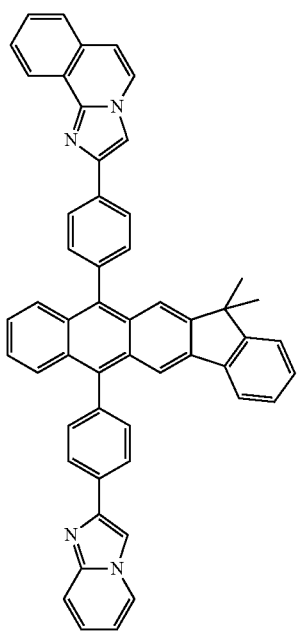
<Compound 57>
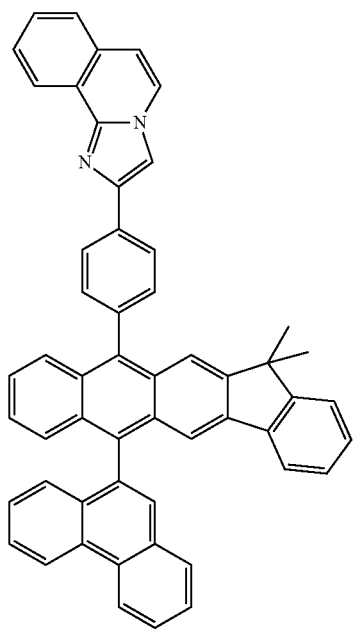
<Compound 56>
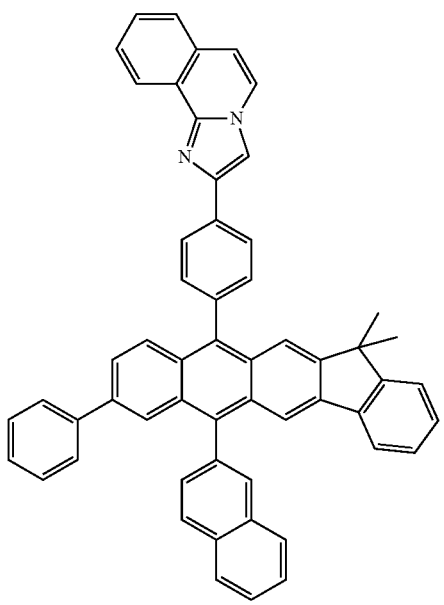
<Compound 58>
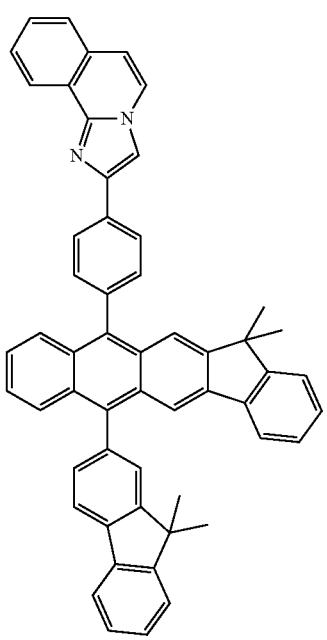

<Compound 59>
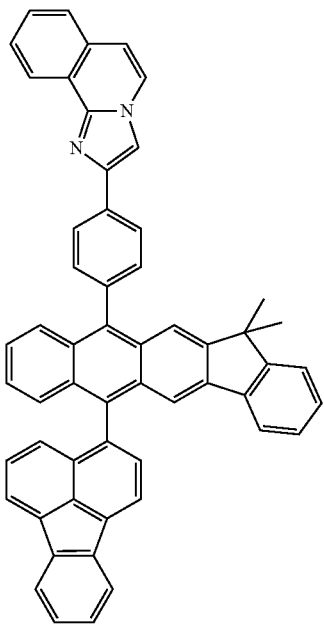
<Compound 60>
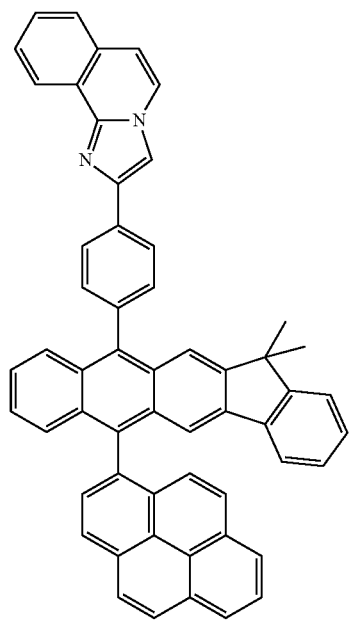
<Compound 61>
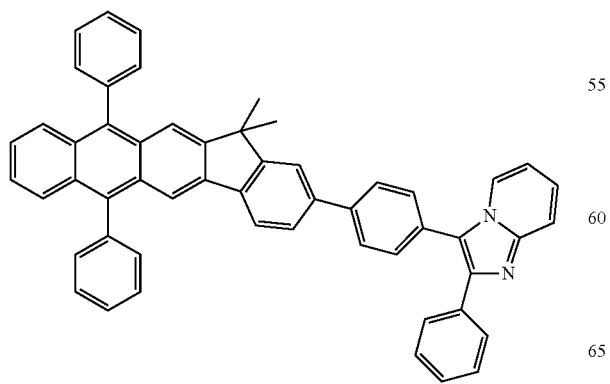
<Compound 62>
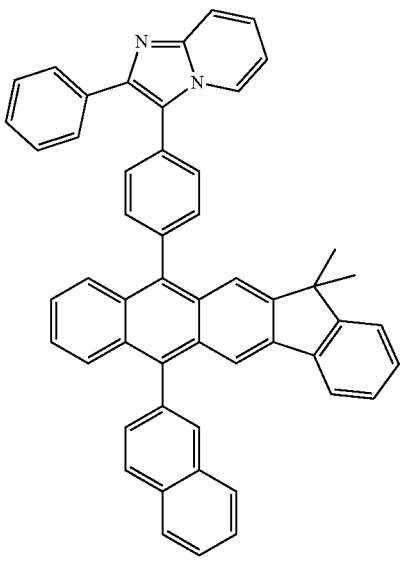
<Compound 63>
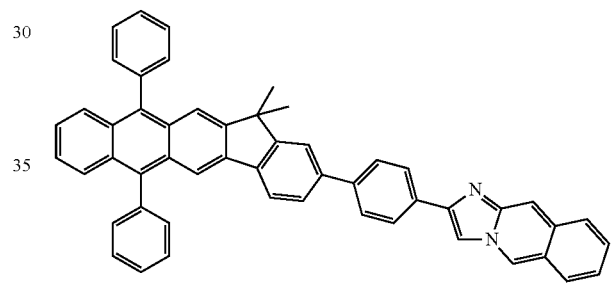
<Compound 64>
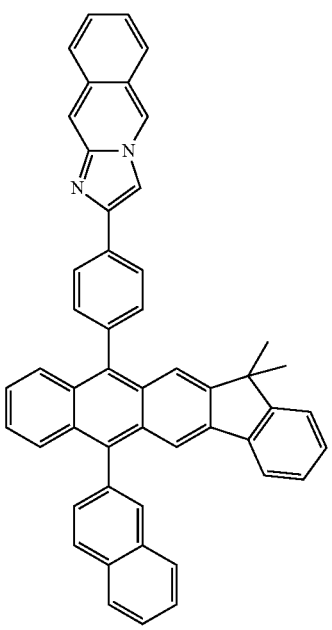

<Compound 65>
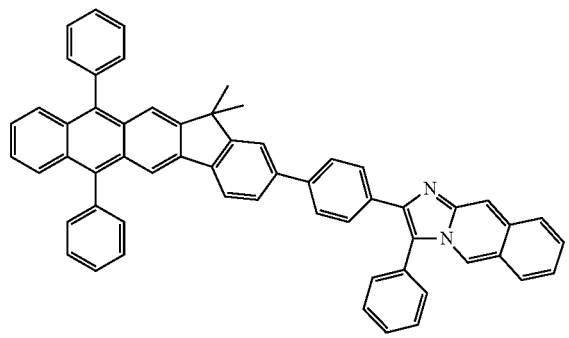
<Compound 66>
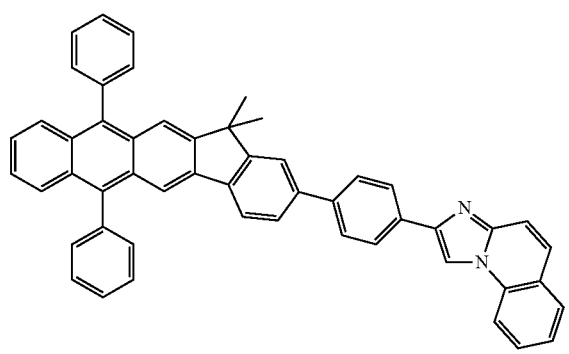
<Compound 67>
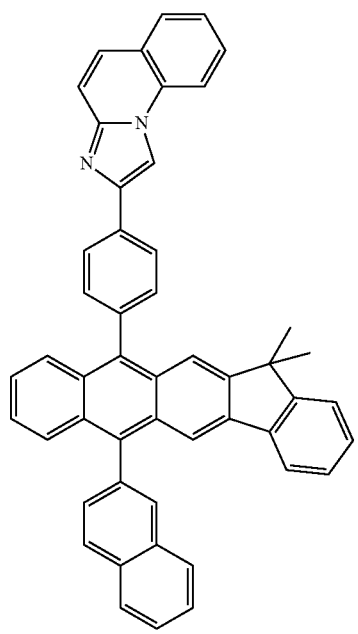
<Compound 68>
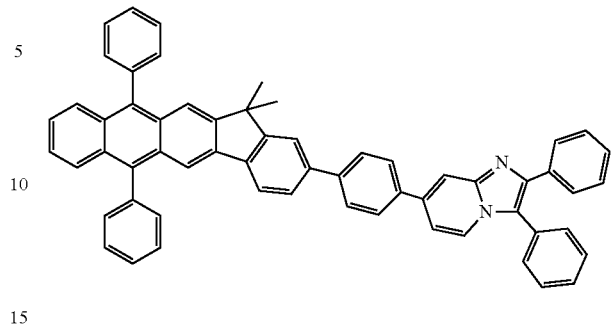
<Compound 69>
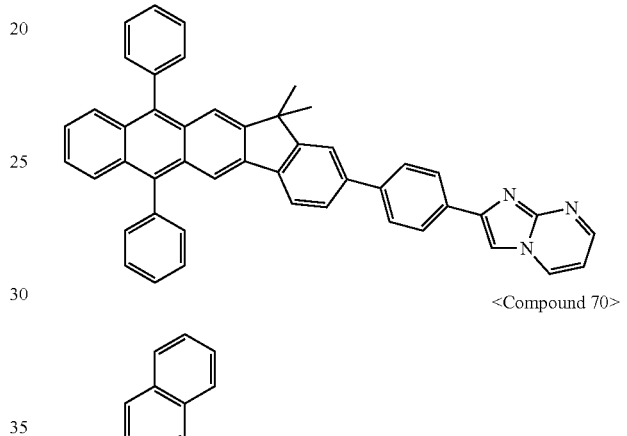
<Compound 70>
<Compound 71>
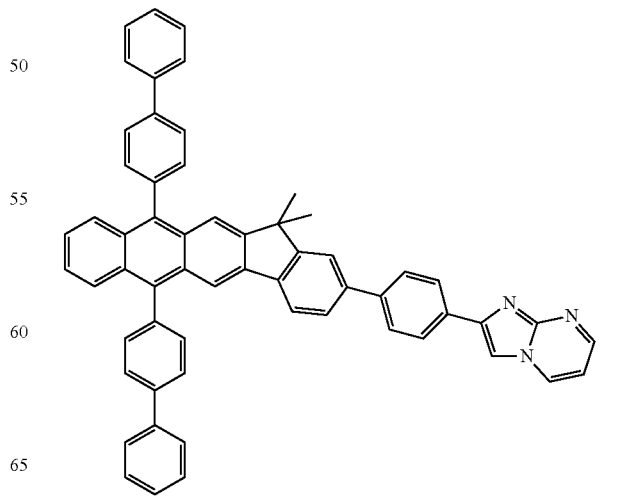

<Compound 72>
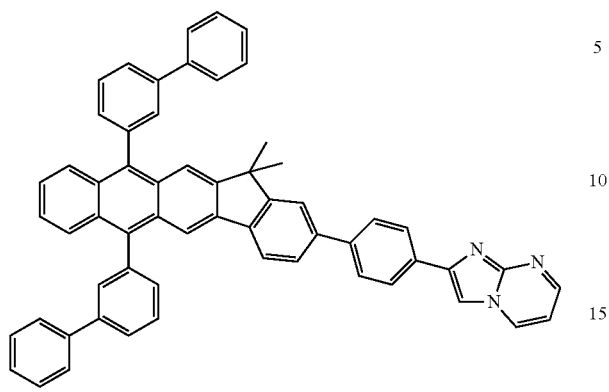
<Compound 73>
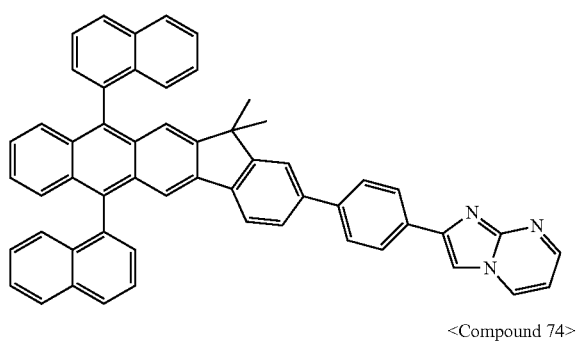
<Compound 74>
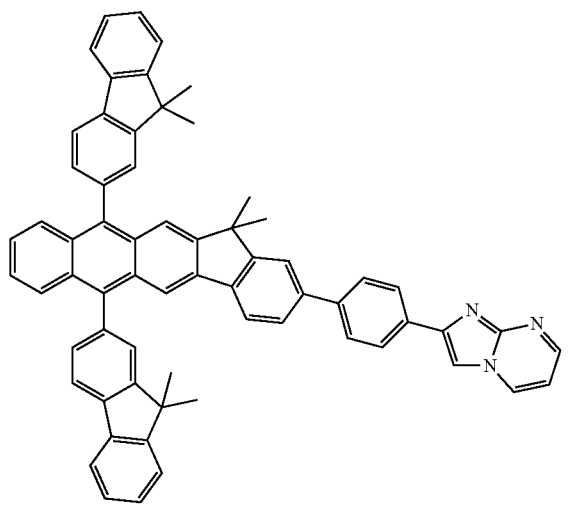
<Compound 75>
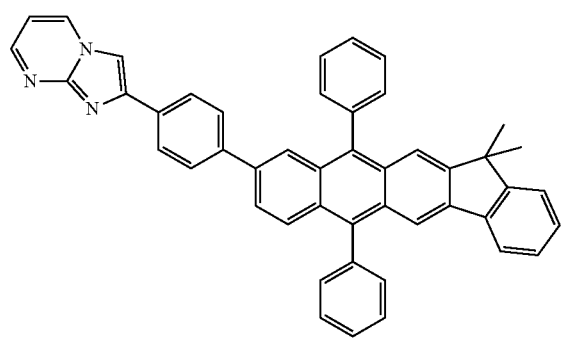
<Compound 76>
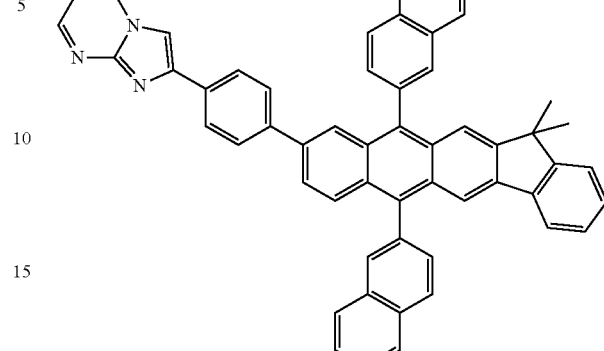
<Compound 77>
<Compound 78>
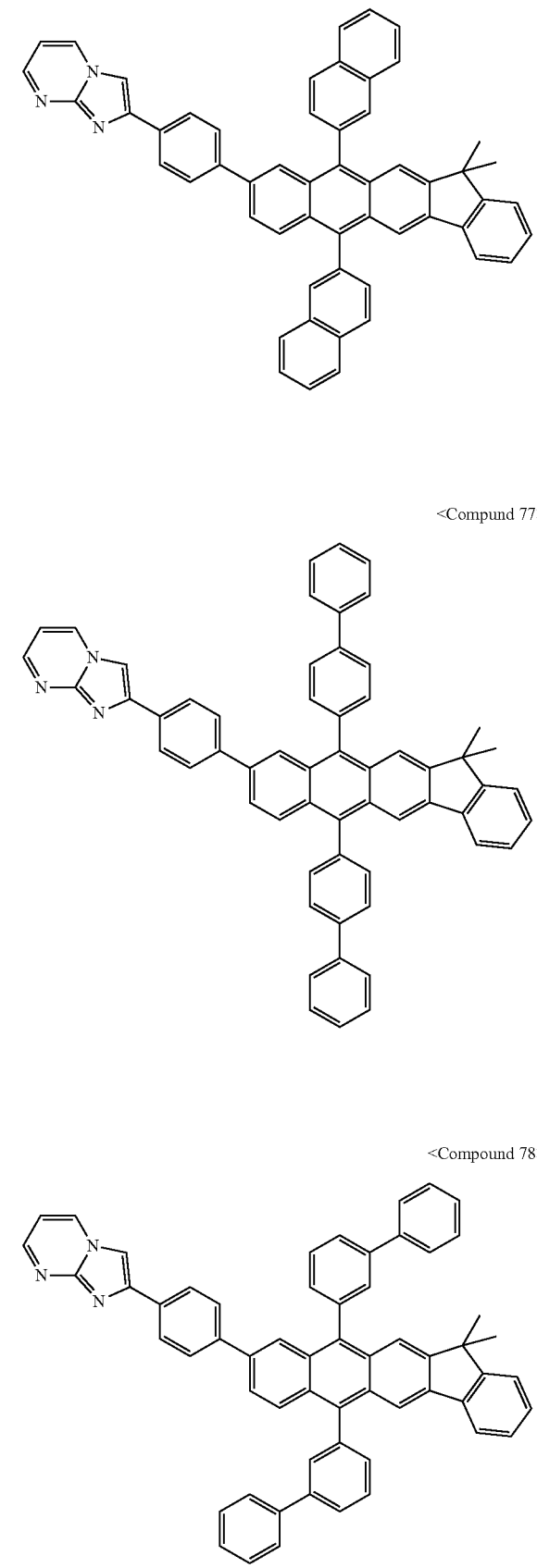

<Compound 79>
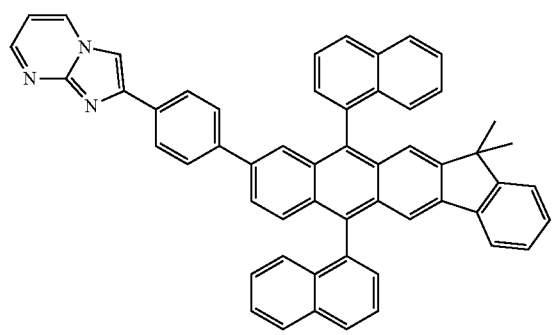
<Compound 82>
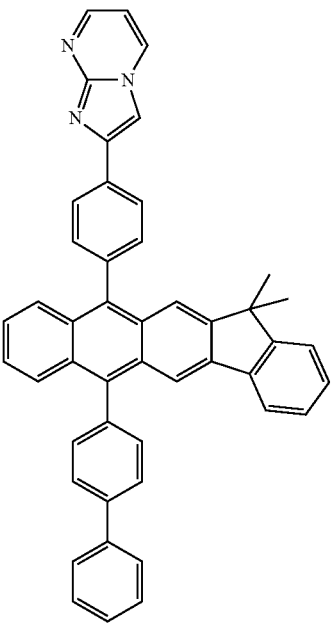
<Compound 80>
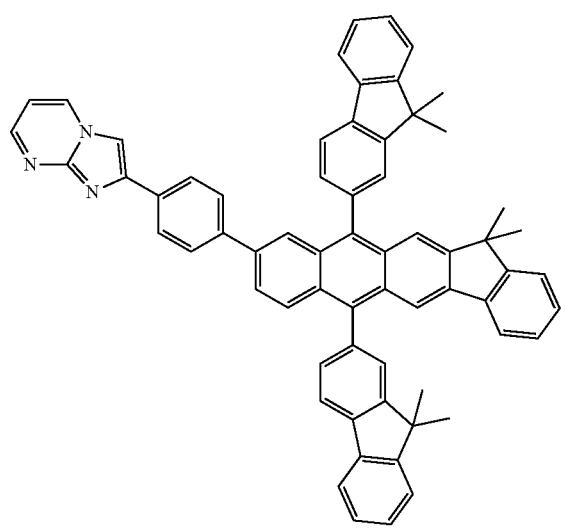
<Compound 81>
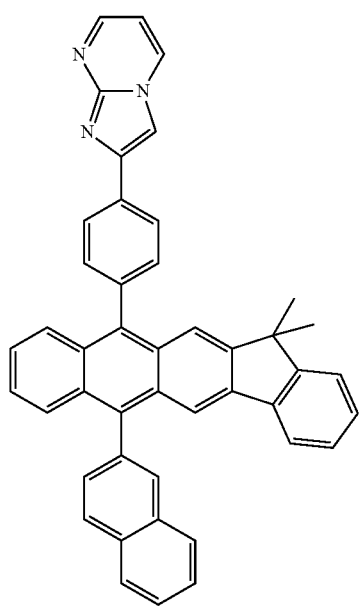
<Compound 83>
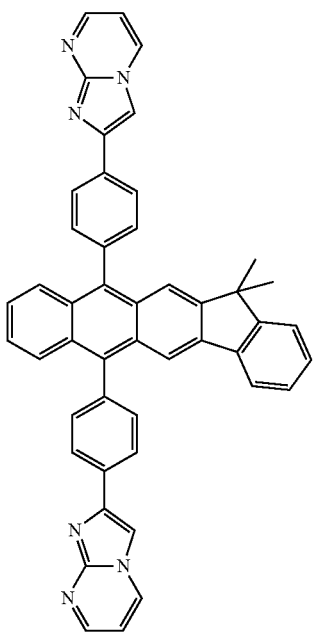

<Compound 84>
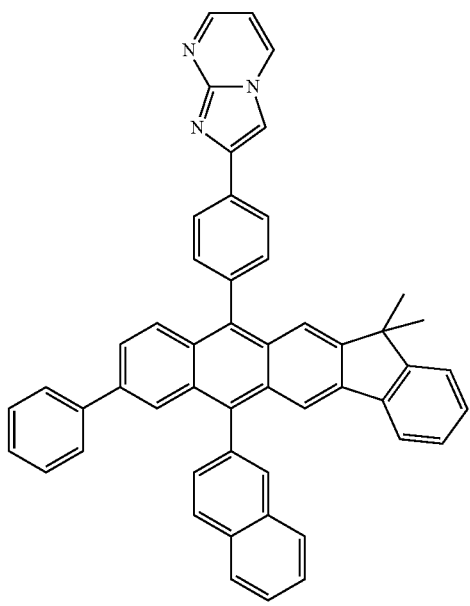
<Compound 85>
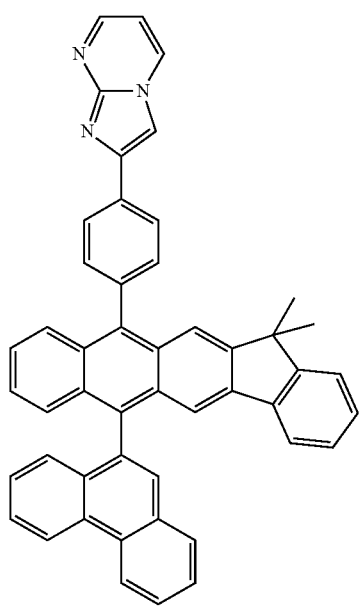
<Compound 86>
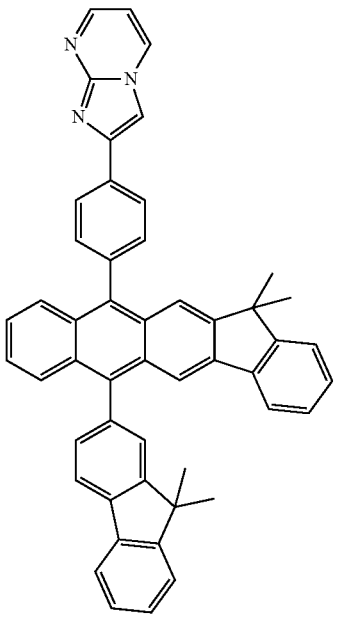
<Compound 87>
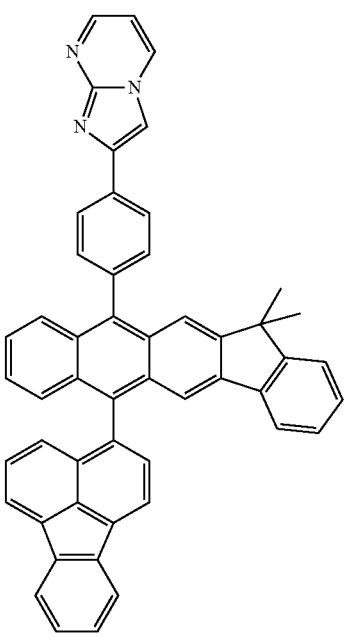

<Compound 88>
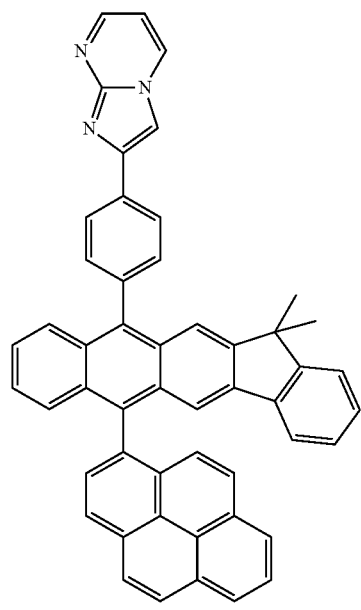
<Compound 89>
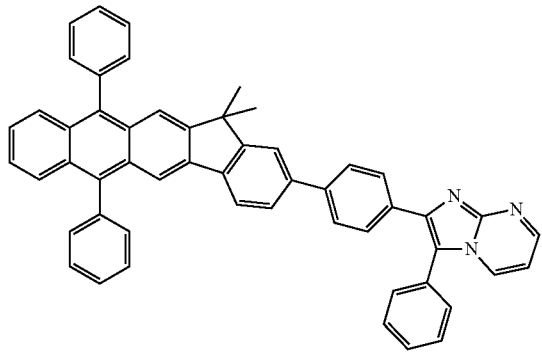
<Compound 90>
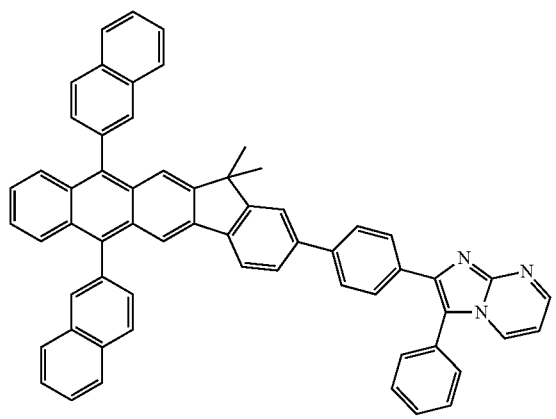
<Compound 91>
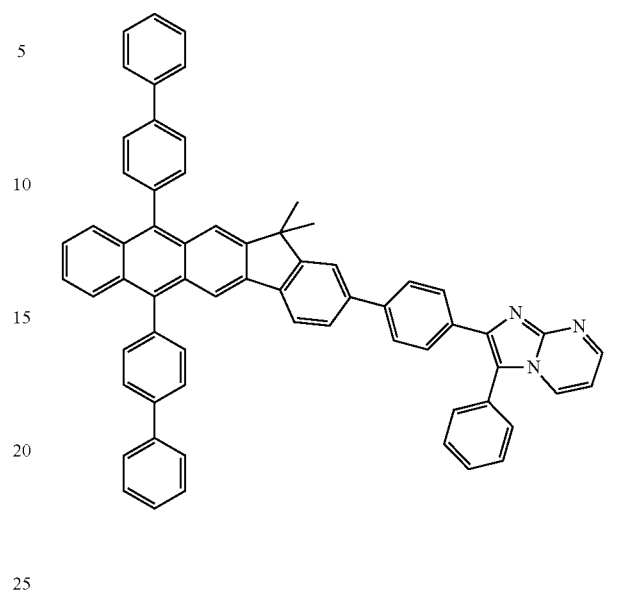
<Compound 92>
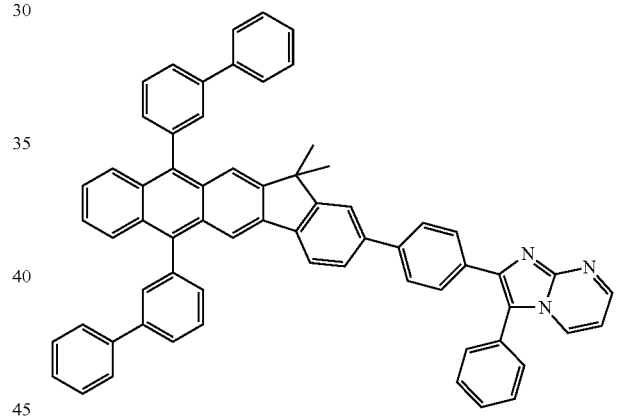
<Compound 93>
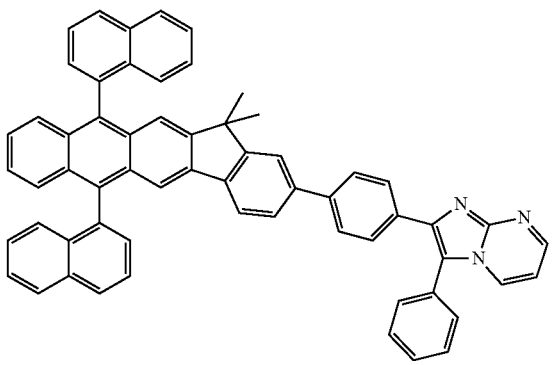

<Compound 94>
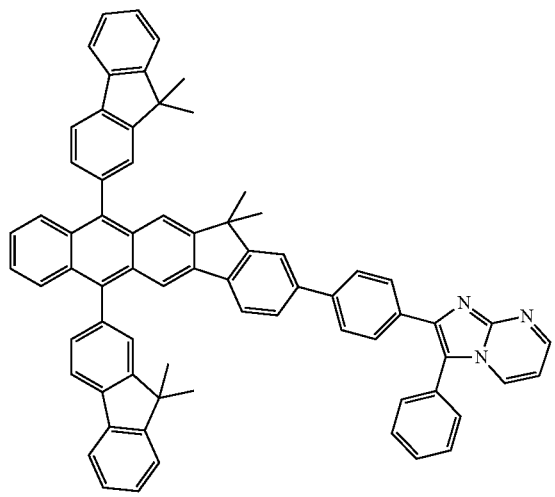
<Compound 95>
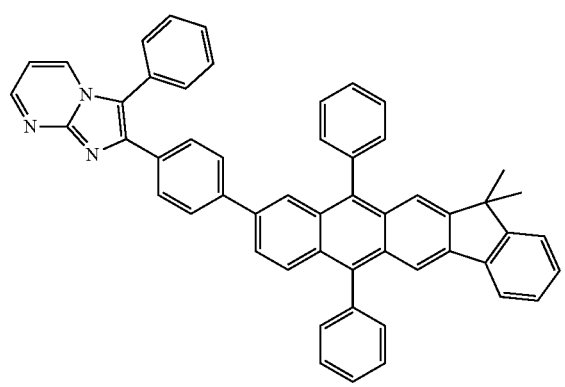
<Compound 96>
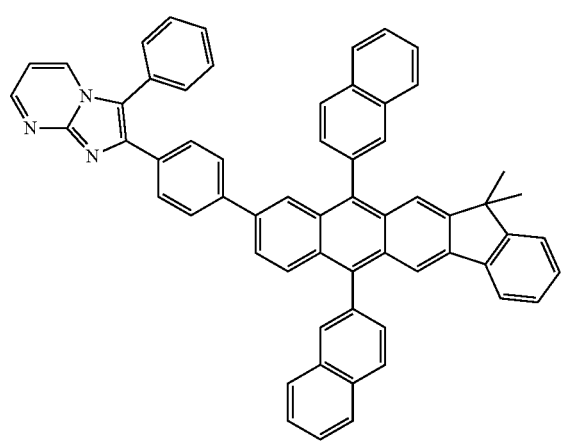
<Compound 97>
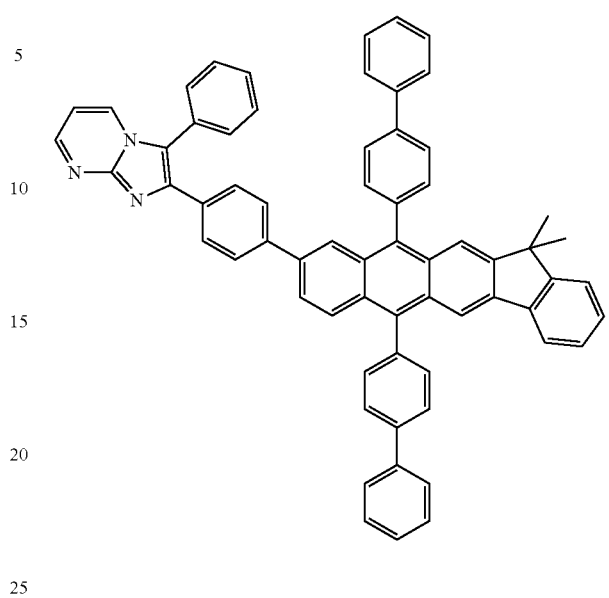
<Compound 98>
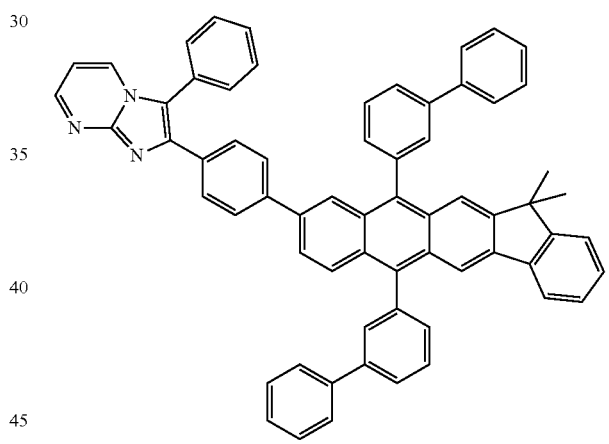
<Compound 99>
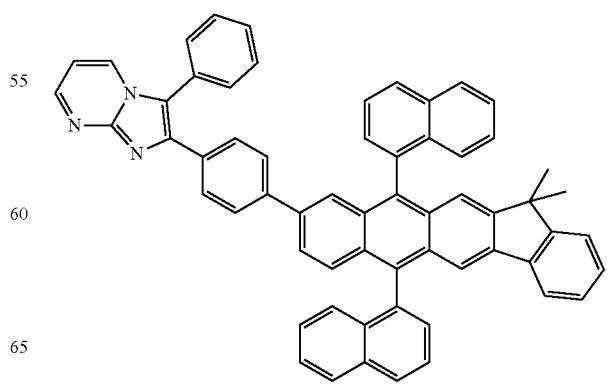

<Compound 100>
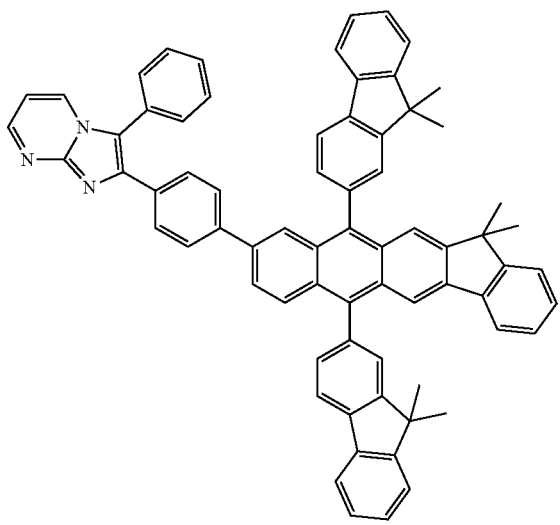

<Compound 101>
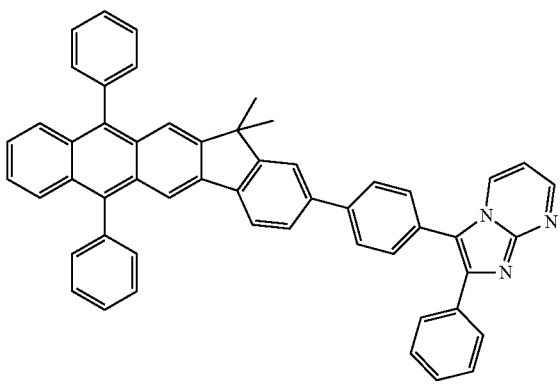

<Compound 102>
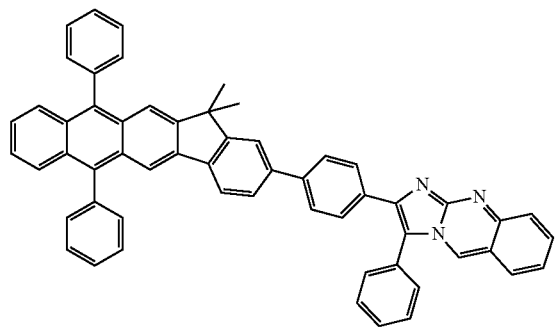

<Compound 103>
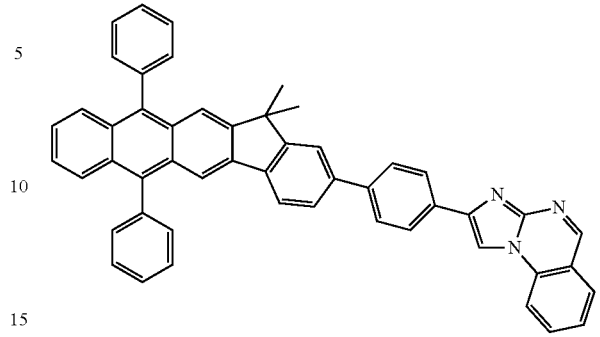

In the expression "substituted or unsubstituted A (A is an arbitrary substituent)," the term "substituted A" denotes "A, in which at least one hydrogen atom of A is substituted with one substituent selected from the group consisting of deuterium, a halogen atom, a hydroxyl group, a cyano group, a nitro group, a carboxyl group or a salt derivative thereof, a sulfonic acid group or a salt derivative thereof, a phosphate group or a salt derivative thereof, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{30}$ cycloalkyl group, a $C_3$-$C_{30}$ cycloalkenyl group, a $C_5$-$C_{30}$ aryl group, a $C_5$-$C_{30}$ aryloxy group, a $C_5$-$C_{30}$ arylthio group, a $C_2$-$C_{30}$ heterocyclic group, a group represented by $N(Q_{101})(Q_{102})$, and a group represented by $Si(Q_{103})(Q_{104})(Q_{105})$." Here, $Q_{101}$ through $Q_{105}$ may be each independently a hydrogen atom, deuterium, a halogen atom, a hydroxyl group, a cyano group, an amino group, a nitro group, a carboxyl group, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{30}$ cycloalkyl group, a $C_3$-$C_{30}$ cycloalkenyl group, a $C_5$-$C_{30}$ aryl group, a $C_5$-$C_{30}$ aryloxy group, a $C_5$-$C_{30}$ arylthio group, or a $C_2$-$C_{30}$ heterocyclic group.

For example, "the substituted A" may denote "A, in which at least one hydrogen atom is substituted with deuterium, a halogen atom, a hydroxyl group, a cyano group, an amino group, a nitro group, a carboxyl group, a methyl group, an ethyl group, a propyl group, a butyl group, a pentyl group, a phenyl group, a pentalenyl group, an indenyl group, a naphtyl group, an azulenyl group, a heptalenyl group, an indacenyl group, an acenaphtyl group, a fluorenyl group, a spiro-fluorenyl group, a phenalenyl group, a phenanthrenyl group, an anthryl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl, benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a benzoxazolyl group, a dibenzofuranyl group, or a dibenzothiophenyl group."

The substituted $C_1$-$C_{30}$ alkyl group denotes a saturated hydrocarbon group having a linear and branched structure in which one hydrogen atom is lacking alkane. Examples of the unsubstituted $C_1$-$C_{30}$ alkyl group may include methyl, ethyl, propyl, isobutyl, sec-butyl, pentyl, iso-amyl, hexyl, and the like. A substituent of the substituted $C_1$-$C_{30}$ alkyl group is described in the description for the "substituted A."

The unsubstituted $C_2$-$C_{30}$ alkenyl group denotes a terminal group containing at least one carbon double bond at the middle or the end of the unsubstituted $C_2$-$C_{30}$ alkyl group. Examples of the unsubstituted $C_2$-$C_{30}$ alkenyl group may include ethenyl, prophenyl, butenyl, pentanyl, hexenyl, heptenyl, octenyl, propadienyl, isoprenyl, allyl, and the like. A substituent of the substituted $C_2$-$C_{30}$ alkenyl group is described in the description for the "substituted A."

The unsubstituted $C_2$-$C_{30}$ alkynyl group denotes a terminal group containing at least one carbon triple bond at the middle or the end of the unsubstituted $C_2$-$C_{60}$ alkyl group. Examples of the unsubstituted $C_2$-$C_{30}$ alkynyl group may include acetylenyl. A substituent of the substituted $C_2$-$C_{30}$ alkynyl group is described in the description for the "substituted A."

The unsubstituted $C_1$-$C_{30}$ alkoxy group has Formula of —OY (Y is the unsubstituted. $C_1$-$C_{30}$ alkyl group) and may be, for example, methoxy, ethoxy, isopropyloxy, butoxy, pentoxy, and the like. A substituent of the substituted $C_1$-$C_{30}$ alkoxy group is described in the description for the "substituted A."

The unsubstituted $C_3$-$C_{30}$ cycloalkyl group denotes a ring-type saturated hydrocarbon group and may be, for example, cyclopropyl, cyclobutyl, cyclopentyl, cyclohexyl, cyclooctyl, and the like. A substituent of the substituted $C_3$-$C_{30}$ cycloalkyl group is described in the description for the "substituted A."

The unsubstituted $C_3$-$C_{30}$ cycloalkenyl group denotes a ring-type unsaturated hydrocarbon group which has at least one carbon double bond and is not an aromatic ring. Examples of the unsubstituted $C_3$-$C_{30}$ cycloalkenyl group may include cyclopropenyl, cyclobutenyl, cyclopentenyl, cyclohexenyl, cycloheptenyl, a 1,3-cyclohexadienyl group, a 1,4-cyclohexadienyl group, a 2,4-cycloheptadienyl group, a 1,5-cyclooctadienyl group, and the like. A substituent of the substituted $C_3$-$C_{60}$ cycloalkenyl group is described in the description for the "substituted A."

The unsubstituted $C_5$-$C_{30}$ aryl group denotes a monovalent group having a $C_5$-$C_{30}$ carbocyclic aromatic system, wherein the monovalent group may be a monocyclic or polycyclic group. In the polycyclic group, at least two rings included therein may be fused to each other. Examples of the unsubstituted $C_5$-$C_{30}$ aryl group may include phenyl, pentalenyl, indenyl, naphtyl, azulenyl, heptalenyl, indacenyl, acenaphtyl, fluorenyl, spiro-fluorenyl, phenalenyl, phenanthrenyl, anthryl, fluoranthenyl, triphenylenyl, pyrenyl, chrysenyl, naphthacenyl, picenyl, perylenyl, pentaphenyl, hexacenyl, and the like. A substituent of the substituted $C_5$-$C_{30}$ aryl group is described in the description for the "substituted A."

The unsubstituted $C_5$-$C_{30}$ aryloxy group denotes a monovalent group, to which carbon atoms of the $C_5$-$C_{30}$ aryl group are attached through an oxygen linking group (—O—). A substituent of the substituted $C_5$-$C_{30}$ aryloxy group is described in the description for the "substituted A."

The unsubstituted $C_5$-$C_{30}$ arylthio group denotes a monovalent group, to which carbon atoms of the $C_5$-$C_{30}$ aryl group are attached through a sulfur linking group (—S—). Examples of the unsubstituted $C_5$-$C_{30}$ arylthio group may include phenylthio, naphtylthio, indanylthio, and indenylthio. A substituent of the substituted $C_5$-$C_{30}$ arylthio group is described in the description for the "substituted A."

The unsubstituted $C_2$-$C_{30}$ heterocyclic group denotes a monocyclic or polycyclic group including at least one ring containing at least one heteroatom selected from the group consisting of N, O, P, and S. In the polycyclic group, at least two rings included therein may be fused to each other. Examples of the unsubstituted $C_2$-$C_{30}$ heterocyclic group may include pyrrolyl, imidazolyl, pyrazolyl, pyridinyl, pyrazinyl, pyrimidinyl, pyridazinyl, isoindolyl, indolyl, indazolyl, purinyl, quinolinyl, benzoquinolinyl, phthalazinyl, naphthyridinyl, quinoxalinyl, quinazolinyl, cinnolinyl, carbazolyl, phenanthridinyl, acridinyl, phenanthrolinyl, phenazinyl, benzooxazolyl, benzoimidazolyl, furanyl, benzofuranyl, thiophenyl, benzothiophenyl, thiazolyl, isothiazolyl, benzothiazolyl, isoxazolyl, oxazolyl, triazolyl, tetrazole, oxadiazolyl, triazinyl, benzooxazolyl, and the like. A substituent of the substituted $C_2$-$C_{30}$ heterocyclic group is described in the description for the "substituted A."

The unsubstituted $C_1$-$C_{30}$ alkylene group denotes a divalent group having a linear and chain structure, in which two hydrogen atoms are lacking alkane. Examples of the unsubstituted $C_1$-$C_{30}$ alkylene group may be understood with reference to the examples of the unsubstituted $C_1$-$C_{30}$ alkyl group. A substituent of the substituted $C_1$-$C_{30}$ alkylene group is described in the description for the "substituted A."

The unsubstituted $C_5$-$C_{30}$ arylene group may denote a divalent group having a $C_5$-$C_{30}$ carbocyclic aromatic system, wherein the divalent group may be a monocyclic or polycyclic group. Examples of the unsubstituted $C_5$-$C_{30}$ arylene group may be understood with reference to the examples of the unsubstituted $C_5$-$C_{30}$ aryl group. A substituent of the substituted $C_5$-$C_{30}$ arylene group is described in the description for the "substituted A."

The unsubstituted divalent $C_2$-$C_{30}$ heterocyclic group denotes a monocyclic or a polycyclic divalent group including at least one ring containing at least one heteroatom selected from the group consisting of N, O, P, and S and may be a monocyclic or a polycyclic group. Examples of the unsubstituted divalent $C_2$-$C_{30}$ heterocyclic group may be understood with reference to the examples of the unsubstituted $C_2$-$C_{30}$ heterocyclic group. A substituent of the substituted divalent $C_2$-$C_{30}$ heterocyclic group is described in the description for the "substituted A."

The condensed-cyclic compound represented by Formula 1 may be synthesized by using a well-known organic synthesis method. The synthesis method of the condensed-cyclic compound may be easily recognized by one of ordinary skill in the art with reference to Examples which will be described later.

The condensed-cyclic compound represented by Formula 1 may be used in an organic light-emitting device. That is, an organic light-emitting device includes a first electrode, a second electrode facing the first electrode, and at least one organic layer interposed between the first electrode and the second electrode, wherein the at least one organic layer includes the condensed-cyclic compound represented by Formula 1.

The organic layer may be an electron injection layer or an electron transport layer and may include the condensed-cyclic compound represented by Formula 1. Also, the organic layer may a functional layer having functions of both electron injection and electron transport and may include the condensed-cyclic compound represented by Formula 1.

The organic light-emitting device may include a hole transport layer including the condensed-cyclic compound represented by Formula 1 or an emission layer including a fluorescent or phosphorescent host.

For example, the organic light-emitting device may have a structure including a first electrode/a hole injection layer/a hole transport layer/an emission layer/an electron transport layer including the condensed-cyclic compound represented by Formula 1/an electron injection layer/a second electrode. However, the present invention is not limited thereto.

Also, the organic layer may be an emission layer in an organic light-emitting device and may include the condensed-cyclic compound represented by Formula 1.

More specifically, the emission layer may only include the condensed-cyclic compound represented by Formula 1 or may further include another compound in addition to the condensed-cyclic compound represented by Formula 1.

For example, the condensed-cyclic compound represented by Formula 1 may be used as a fluorescent host or a phosphorescent host in the emission layer. In this case, the emission layer may further include a fluorescent dopant or a phosphorescent dopant. That is, the emission layer may include the condensed-cyclic compound represented by Formula 1 functioning as a fluorescent host and a fluorescent dopant or may include the condensed-cyclic compound represented by Formula 1 functioning as a phosphorescent host and a phosphorescent dopant. Also, the condensed-cyclic compound represented by Formula 1 may be used as a fluorescent dopant of the emission layer. In this case, the emission layer may further include a fluorescent host or a phosphorescent host, in addition to the condensed-cyclic compound represented by Formula 1. That is, the emission layer may include the condensed-cyclic compound represented by Formula 1 functioning as a fluorescent dopant, a phosphorescent host, or a fluorescent host.

The organic light-emitting device may include at least one selected from the group consisting of a hole injection layer, a hole transport layer, an electron blocking layer, a hole blocking layer, an electron transport layer, and an electron injection layer between the first electrode and the second electrode, in addition to the emission layer.

The at least one layer interposed between the first electrode and the second electrode may be formed by deposition or a wet process. For example, at least one selected from the group consisting of a hole injection layer, a hole transport layer, an emission layer, a hole blocking layer, an electron transport layer, and an electron injection layer between the first electrode and the second electrode may be formed by deposition or a wet process.

In the specification, "wet process" is a process for providing a mixture obtained by mixing a predetermined material and a predetermined solvent to a predetermined substrate, drying and/or thermal treating the predetermined substrate so as to remove at least part of the predetermined solvent, and thereby forming a film including the predetermined material on the substrate.

An organic layer including the condensed-cyclic compound represented by Formula 1 may be formed by a general vacuum deposition of a wet process. For example, the condensed-cyclic compound represented by Formula 1 and the mixture including the solvent are provided to an electron transport layer region by using spin coating, spraying, inkjet printing, dipping, casting, gravure coating, bar coating, roll coating, wirebar coating, screen coating, flexo coating, offset coating, or laser transferring and then the mixture provided to the electron transport layer region is dried and/or heat treated so as to remove at least part of the solvent. Thus, the electron transport layer including the condensed-cyclic compound represented by Formula 1 may be formed.

Also, a layer including the condensed-cyclic compound represented by Formula 1 may be formed on the base film by using a wet process and the layer may be transferred on the electron transport layer region by laser transferring using laser FIG. 1 is a cross-sectional view of an organic light-emitting device 10 according to an embodiment of the present invention. Hereinafter, a structure and a manufacturing method of the organic light-emitting device 10 will be described with reference to FIG. 1.

The organic light-emitting device 10 includes a substrate 11, a first electrode 12, a hole injection layer 13, a hole transport layer 14, an emission layer 15, an electron transport layer 16, an electron injection layer 17, and a second layer 18 sequentially in this order.

The substrate 11 may be a substrate used in a general organic light-emitting device and may be, for example, a glass substrate or a transport plastic substrate having excellent mechanical strength, thermal stability, transparency, surface smoothness, easy-handling, and waterproofness.

The first electrode 12 may be formed by providing a first electrode material on the substrate 11 using deposition or sputtering. When the first electrode 12 is an anode, the first electrode material may be selected from materials having a high work function so as to facilitate hole injection. The first electrode 12 may be a reflective electrode or a transmissive electrode. Examples of the first electrode material may include indium-tin oxide (ITO), Indium-zinc-oxide (IZO), tin oxide ($SnO_2$), and zinc oxide (ZnO). Also, when magnesium (Mg), aluminum (Al), aluminum-lithium (Al—Li), calcium (Ca), magnesium-indium (Mg—In), or magnesium-silver (Mg—Ag) is used, the first electrode 12 may be formed as a reflective electrode. The first electrode 12 may include two different materials. The structure of the first electrode 12 may vary and, for example, the first electrode 12 may be formed to have a two-layered structure including two different materials.

The hole injection layer 13 is formed on the first electrode 12.

The hole injection layer 13 may be formed on the first electrode 12 by using various methods such as vacuum deposition, a wet process, or laser transferring.

When the hole injection layer 13 is formed by using a vacuum deposition, the deposition condition may vary according to a compound used as a material for a hole injection layer, a structure of a desired hole injection layer, and thermal characteristics. For example, the deposition condition may be, but is not limited to, deposition temperature of about 100 to about 500° C., a degree of vacuum of about $10^{-8}$ to about $10^{-3}$ torr, and deposition speed of about 0.01 to about 100 Å/sec.

When the hole injection layer 13 is formed by using spin coating as a wet process, the coating condition may vary according to a compound used as a material for a hole injection layer, a structure of a desired hole injection layer, and thermal characteristics. For example, the coating condition may be, but is not limited to, coating speed of about 2000 rpm to about 5000 rpm and heat treatment temperature for removing a solvent after coating of about 80 to about 200° C.

The condensed-cyclic compound may be used as the material for a hole injection layer. Also, the material for a hole injection layer may include at least one selected from the group consisting of the condensed-cyclic compound and a well-known material for a hole injection layer and may include, for example, a phthalocyanine compound such as copper phthalocyanine, m-MTDATA (refer to Formula below), TDATA (refer to Formula below), 2-TNATA (refer to Formula below), Polyaniline/Dodecylbenzenesulfonic acid (Pani/DBSA), Poly(3,4-ethylenedioxythiophene)/Poly(4-styrenesulfonate) (PEDOT/PSS), Polyaniline/Camphor sulfonicacid (Pani/CSA), or Polyaniline/Poly(4-styrenesulfonate) (PANI/PSS). However, the present invention is not limited thereto.

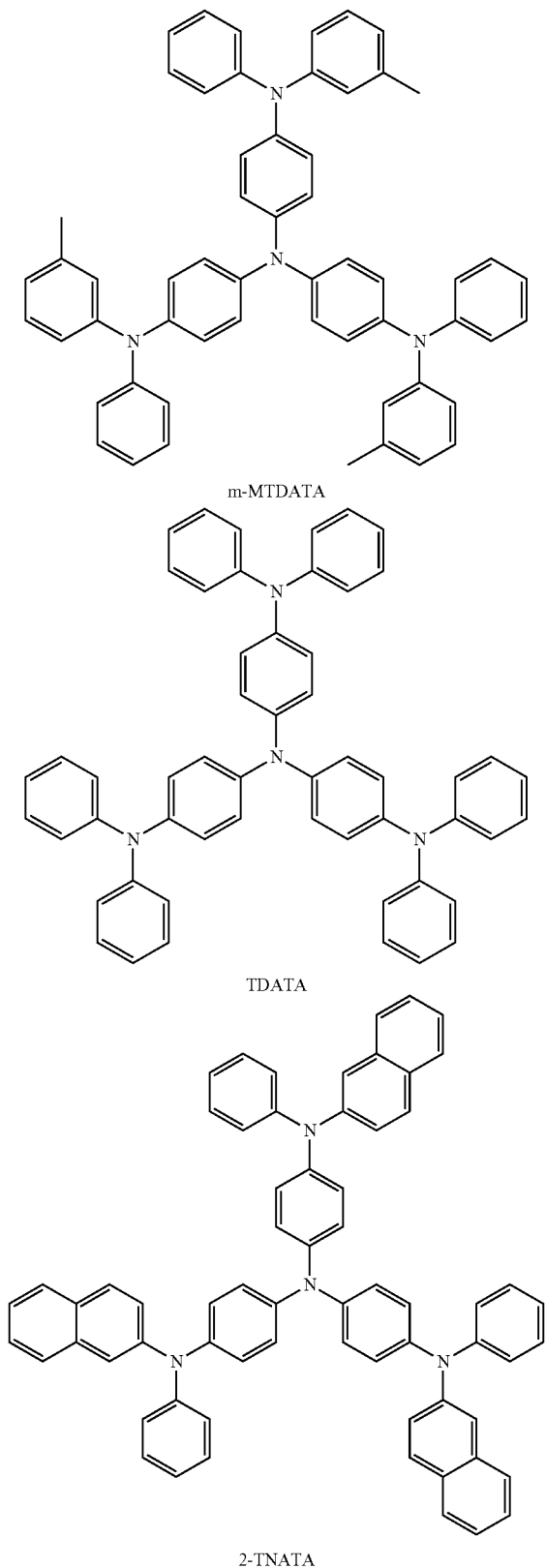

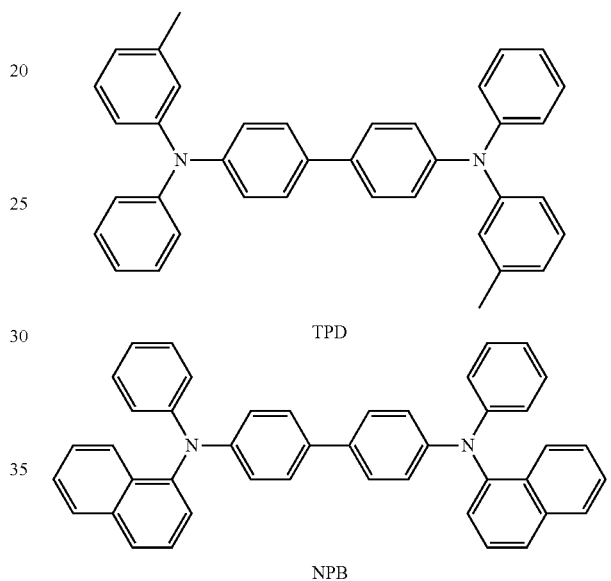

A thickness of the hole injection layer 13 may be about 100 Å to about 10000 Å, for example, about 100 Å to about 1000 Å. When the thickness of the hole injection layer 13 is in the above range, satisfiable hole injection characteristics may be obtained without a substantial increase of a driving voltage.

Then, the hole transport layer 14 is formed on the hole injection layer 13 by using vacuum deposition, a wet process, and laser transferring. When the hole transport layer 14 is formed by vacuum deposition and spin coating, the deposition condition and coating condition may vary according to a used compound. However, in general, the conditions may be almost similar to the condition for forming the hole injection layer 13.

The hole transport layer 14 may include a well-known material for a hole transport layer, for example, TPD (refer to Formula below) and NPB (refer to Formula below).

A thickness of the hole transport layer 14 may be about 50 Å to about 1000 Å, for example, about 100 Å to about 800 Å. When the thickness of the hole transport layer 14 is in the above range, satisfiable hole transport characteristics may be obtained without a substantial increase of a driving voltage.

Instead of the hole injection layer 13 and the hole transport layer 14, a function layer (not illustrated) simultaneously having a hole injection function and a hole transport function may be formed. A material for forming the function layer simultaneously having a hole injection function and a hole transport function may be selected from well-known materials.

At least one selected from the group consisting of the hole injection layer 13, the hole transport layer 14, and the functional layer simultaneously having a hole injection function and a hole transport function may further include a charge-generation material for improving conductivity of a layer, in addition to the condensed-cyclic compound represented by Formula 1, a well-known hole injection material, and a well-known hole transport material.

Examples of the charge-generation material may include a p-dopant. Examples of the p-dopant may include, but are not limited to, a quinone derivative such as tetracyanoquinonedimethan (TCNQ) or 2,3,5,6-tetrafluoro-tetracyano-1,4-benzonquinonedimethane (F4TCNQ); a metal oxide such as a tungsten oxide or a molybdenum oxide; and a cyano group containing a compound such as hexanitrile hexaazatriphenylene.

When the hole injection layer 13, the hole transport layer 14, or the functional layer simultaneously having a hole injection function and a hole transport function further includes the charge-generation material, the charge-generation material is homogeneously or non-homogeneously dispersed in the layers.

The emission layer 15 may be formed on the hole transport layer 14 or the functional layer simultaneously having a hole injection function and a hole transport function by using vacuum deposition, a wet process, or laser transferring. When the emission layer 15 is formed by vacuum deposition and spin coating, the deposition condition may vary according to a used compound. However, in general, the conditions may be almost similar to the condition for forming the hole injection layer 13.

The emission layer 15 may include at least one selected from the group consisting of the condensed-cyclic compound of Formula 1 and well-known phosphorescent host, fluorescent host, phosphorescent dopant, and fluorescent dopant. When the emission layer 15 includes the condensed-cyclic compound represented by Formula 1, the condensed-cyclic compound may function as a phosphorescent host, a fluorescent host, a phosphorescent dopant, or a fluorescent dopant.

Examples of the well-known host may include 4,4'-N,N'-dicarbazole-biphenyl (CBP), 9,10-di-naphthalene-2-yl-anthracene (AND, refer to Formula below), TPBI (refer to Formula below), TBADN (refer to Formula below), E3 (refer to Formula below). However, the present invention is not limited thereto.

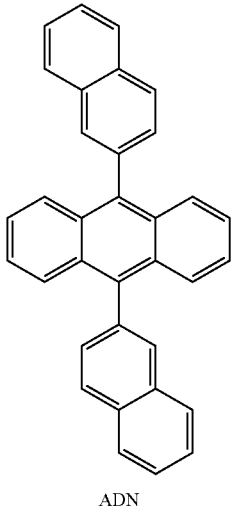

ADN

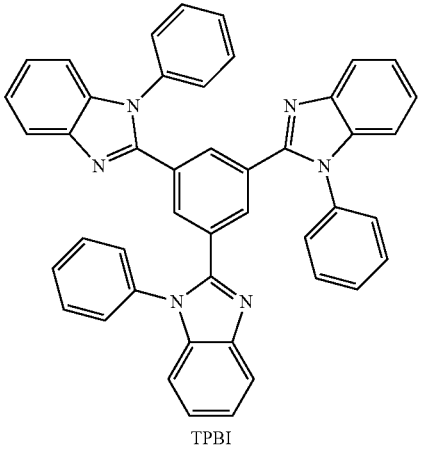

TPBI

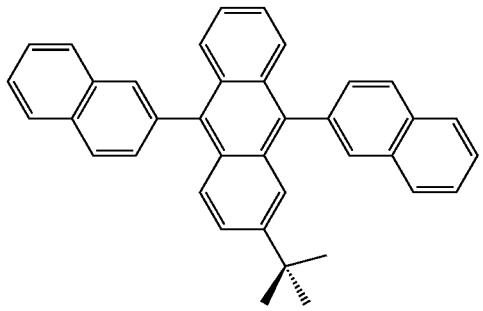

TBADN

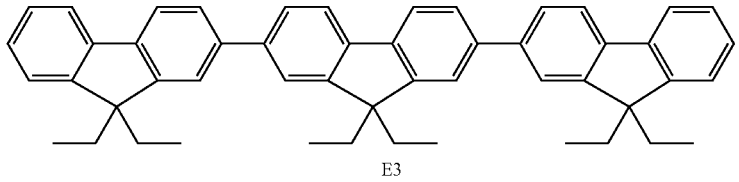

E3

At least one of the fluorescent dopant and the phosphorescent dopant may be used as a dopant. The phosphorescent dopant may be an organic metal complex including Ir, Pt, Os, Re, Ti, Zr, Hf, or combinations including at least two of Ir, Pt, Os, Re, Ti, Zr, and Hf. However, the present invention is not limited thereto.

As a red dopant, PtOEP (refer to Formula below), Ir (piq)$_3$ (refer to Formula below), or Btp$_2$Ir(acac) (refer to Formula below) may be used. However, the present invention is not limited thereto.

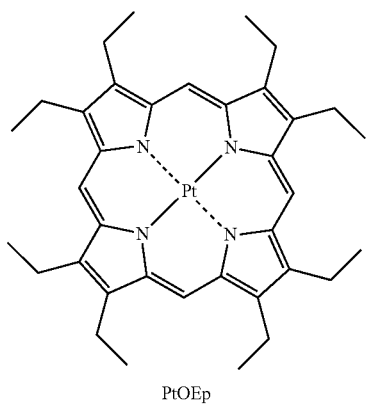

PtOEp

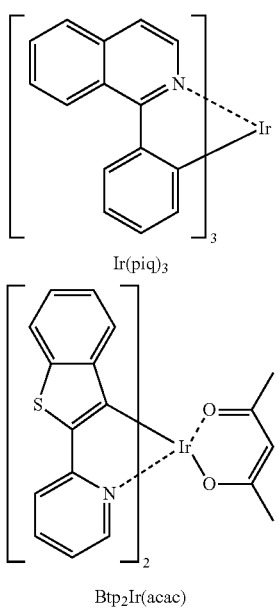

Ir(piq)₃

Btp₂Ir(acac)

As a green dopant, Ir(ppy)₃ (ppy=phenyl-pyridines, refer to Formula below), Ir(ppy)₂(acac) (refer to Formula below), or Ir(mpyp)₃ (refer to Formula below) may be used. However, the present invention is not limited thereto.

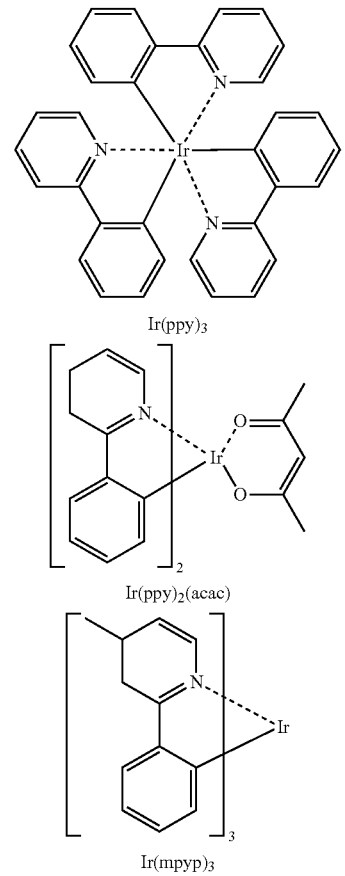

Ir(ppy)₃

Ir(ppy)₂(acac)

Ir(mpyp)₃

As a blue dopant, F₂Irpic (refer to Formula below), (F₂ppy)₂Ir(tmd) (refer to Formula below), Ir(dfppz)₃ (refer to Formula below), DPVBi (refer to Formula below), 4,4'-bis(4-diphenylaminosteril) biphenyl (DPAVBi, refer to Formula below), or 2,5,8,11-tetra-tert-butylpherylene (TBPe, refer to Formula below) may be used. However, the present invention is not limited thereto.

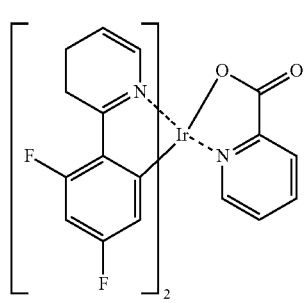

F₂Irpic

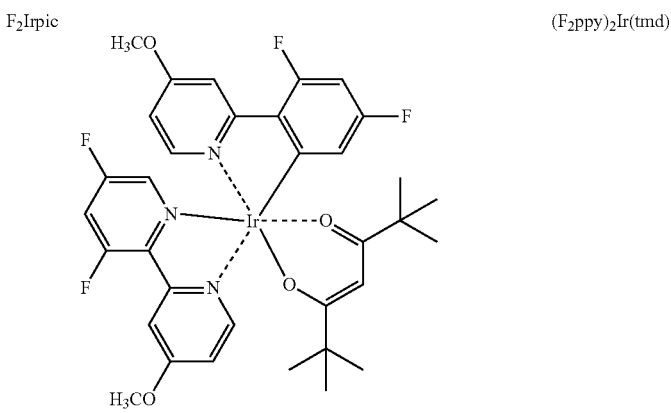

(F₂ppy)₂Ir(tmd)

Ir(dfppz)₃

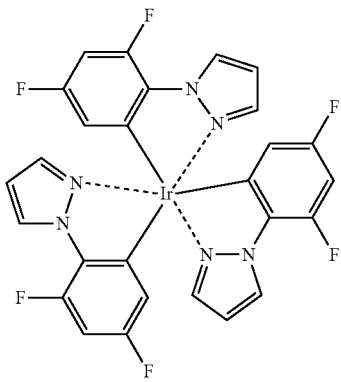

DPVBi

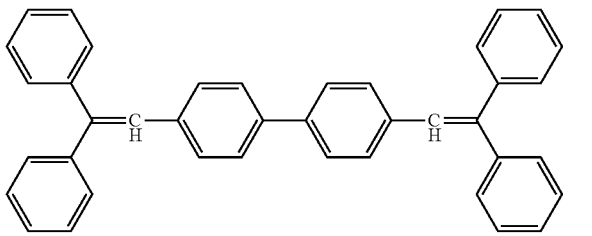

DPAVBi

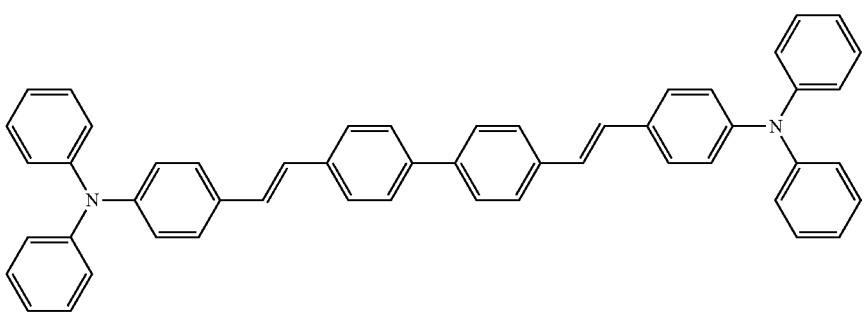

TBPe

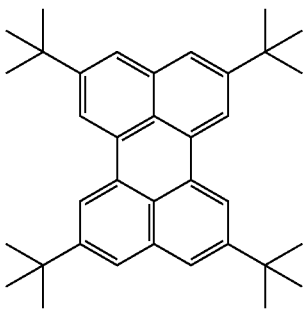

When the emission layer 15 includes a host and a dopant, an amount of the dopant may be generally in the range of about 0.01 to about 15 parts by weight based on 100 parts by weight of the host. However, the present invention is not limited thereto.

A thickness of the emission layer 15 may be about 100 Å to about 1000 Å, for example, about 200 Å to about 600 Å. When the thickness of the emission layer 15 is in the above range, excellent emission characteristic may appear without a substantial increase of a driving voltage.

When the phosphorescent dopant is included in the emission layer 15, a hole blocking layer (not illustrated) may be formed between the emission layer 15 and the hole transport layer 16 by using vacuum deposition, a wet process, or laser transferring so as to prevent triplet excitons or holes from being diffused to the electron transport layer 16. When the hole blocking layer is formed by using vacuum deposition and spin coating, the conditions thereof may vary according to a used compound. However, in general, the conditions may be almost similar the condition for forming the hole injection layer 13. A well-known hole blocking material may be used. Examples of the well-known hole blocking material may include an oxadiazole derivative, a triazole derivative, and a phenanthroline derivative.

A thickness of the hole blocking layer may be about 50 Å to about 1000 Å, for example, about 100 Å to about 300 Å. When the thickness of the hole blocking layer is in the above range, excellent hole blocking characteristic may appear without a substantial increase of a driving voltage.

Then, the electron transport layer 16 is formed by using vacuum deposition, a wet process, or laser transferring. When the electron transport layer 16 is formed by using vacuum deposition or spin coating, the conditions thereof may vary according to a used compound. However, in general, the conditions may be almost similar to the condition for forming the hole injection layer 13. The condensed-cyclic compound represented by Formula 1 may be used as a material for forming the electron transport layer 16. Also, the electron transport layer 16 may further include a well-known electron transport material to stably transport electrons injected from a cathode. Examples of the well-known transport material may include a quinoline derivative, in particular, tris(8-quinolinolate)aluminum ($Alq_3$), TAZ (refer to Formula below), Balq (refer to Formula below), beryllium bis benzoquinolin-10-olate ($Bebq_2$). However, the present invention is not limited thereto.

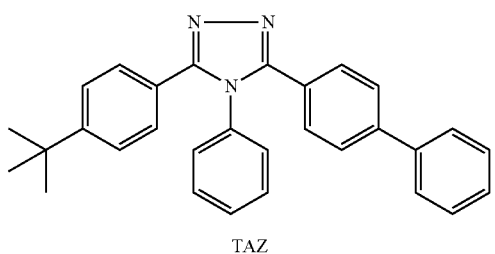

TAZ

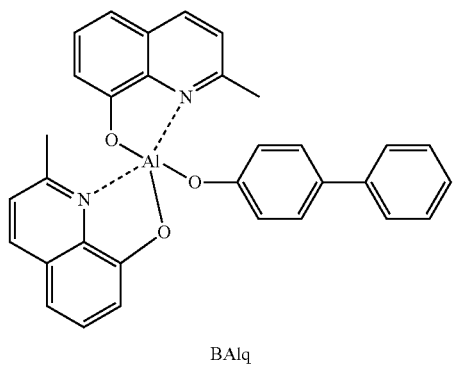

BAlq

A thickness of the electron transport layer 16 may be about 100 Å to about 1000 Å, for example, about 150 Å to about 500 Å. When the thickness of the electron transport layer 16 is in the above range, excellent electron transport characteristic may be obtained without a substantial increase of a driving voltage.

Also, the electron transport layer 16 may include an electron transport organic compound and a metal-containing material. Examples of the electron transport organic compound may include, but are not limited to, 9,10-di(naphthalene-2-yl)anthracene (AND); and an anthracene-based compound such as a compound 301 or 302 below:

<Compound 301>

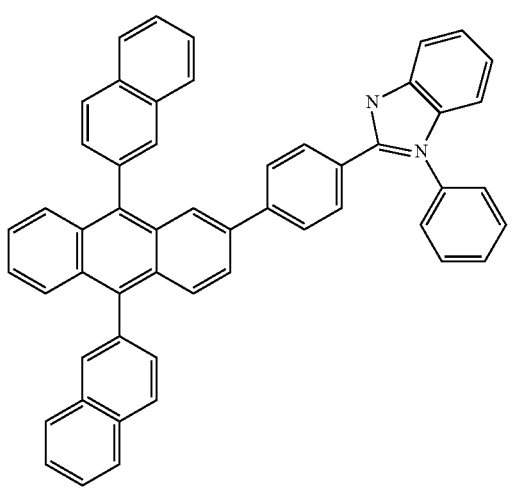

<Compound 302>

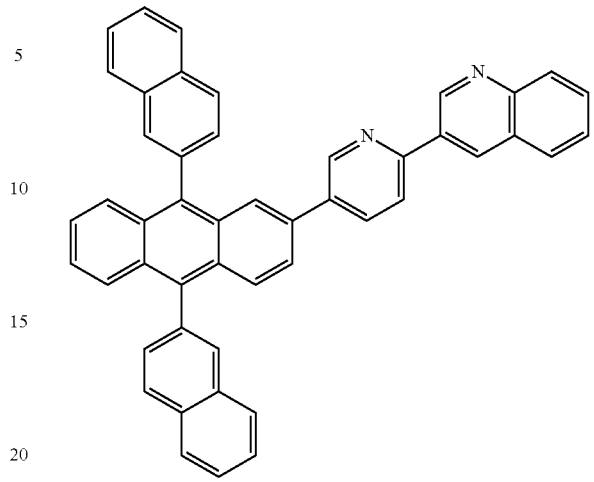

The metal-containing material may include a Li complex. Examples of the Li complex may include, but are not limited to, lithium quinolate (LiQ) or compound 303 below:

<Compound 303>

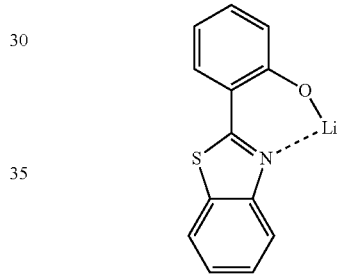

Also, the electron injection layer 17, which facilitates electron injection from a cathode, may be formed on the electron transport layer 16. A material for forming the electron injection layer 17 may include a well-known arbitrary material for forming the electron injection layer, such as LiF, NaCl, CsF, $Li_2O$, or BaO. The deposition condition of the electron injection layer 17 may vary according a used compound. However, in general, the condition may be almost similar to the condition for forming the hole injection layer 13.

A thickness of the electron injection layer 17 may be about 1 Å to about 100 Å, for example, about 3 Å to about 90 Å. When the thickness of the electron injection layer 17 is in the above range, satisfiable hole injection characteristics may be obtained without a substantial increase of a driving voltage.

The second electrode 18 as a transmissive electrode may be formed on the electron injection layer 17. The second electrode 18 may be a cathode, which is an electrode injection electrode. Here, a metal for forming the second electrode 18 may include a metal having low work function, an alloy, an electric conducting compound, and mixtures thereof. More specifically, the transmissive electrode may be obtained by forming a thin film by using lithium (Li), magnesium (Mg), aluminum (Al), aluminum-lithium (Al—Li), calcium (Ca), magnesium-indium (Mg—In), or magnesium-silver (Mg—Ag). In order to obtain a top-emission light-emitting device, the transmissive electrode may be formed by using ITO or IZO.

The organic light-emitting device may be included in the flat panel display apparatus including the transistor. Accordingly, a flat panel display apparatus includes an organic light-emitting device including a transistor including a source electrode, a drain electrode, a gate, and an active layer, and an organic layer including the condensed-cyclic compound represented by Formula 1 above, wherein in the organic light-emitting device, the first electrode is electrically connected to the source electrode or the drain electrode. The active layer of the transistor may vary and may be, for example, an amorphous silicon layer, a crystallized silicon layer, an organic semiconductor layer, or an oxide semiconductor layer.

Hereinafter, an organic light-emitting device according to the present invention will be described more specifically with reference to the following Synthesis Examples and Examples. The following Synthesis Examples and Examples are for illustrative purposes and are not intended to limit the scope of the invention.

EXAMPLES

Synthesis Example 1

Synthesis of Compound 2

Compound 2 was synthesized according to Reaction Formula 1 below:

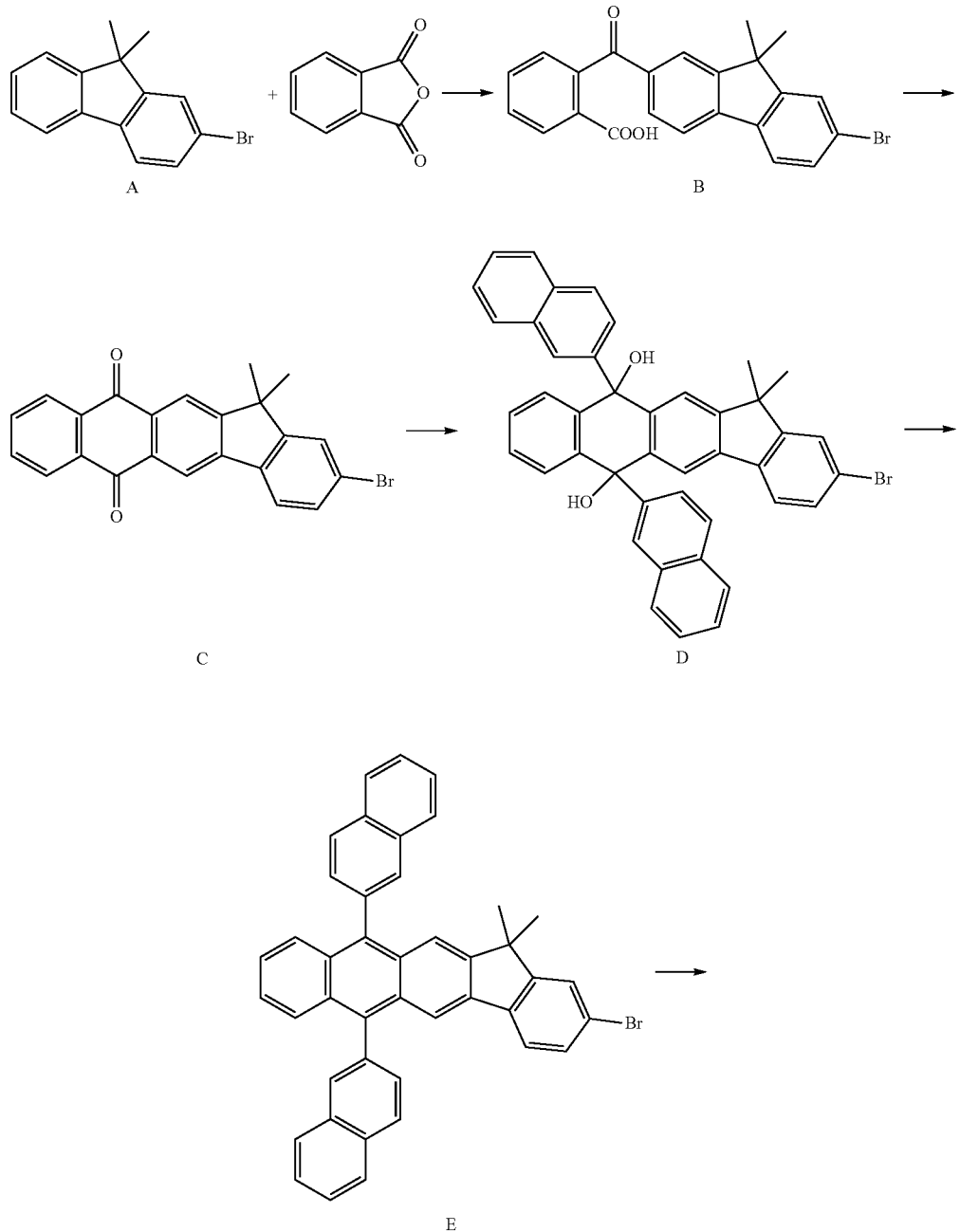

-continued

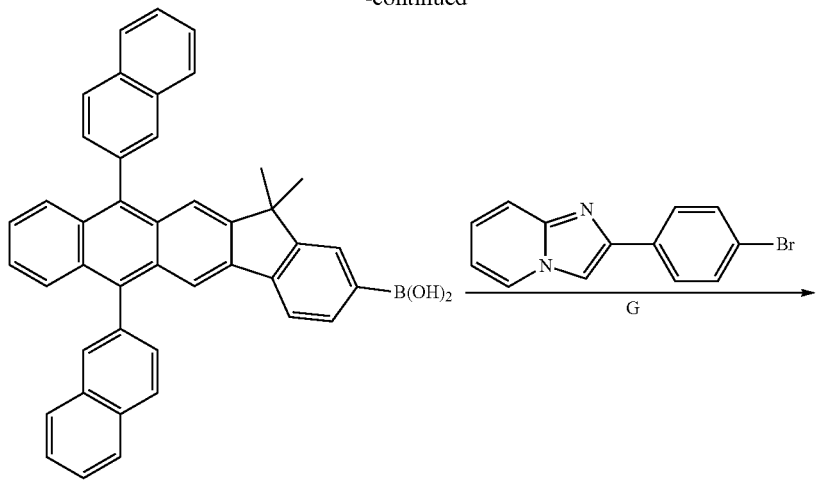

F

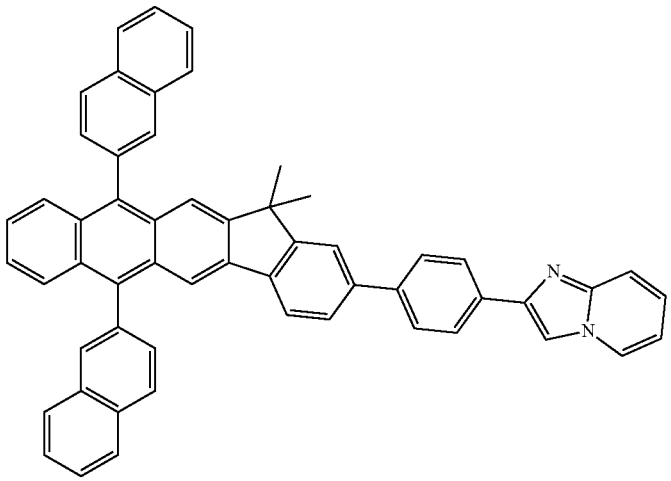

Compound 2

1) Synthesis of Intermediate B 27.3 g (0.1 mol) of intermediate A and 16.3 g (0.11 mol) of phthalic anhydride were put in a flask and dichloromethane was added to the flask. 20 g (0.15 mol) of aluminum chloride was gradually added to the flask at 0° C. and then was stirred for 12 hours at room temperature so as to obtain a reaction mixture. After the reaction was completed, distilled water was slowly added to the reaction mixture and was extracted using dichloromethane. Then, a solvent was removed and a solid was obtained. The obtained solid was washed using hexane, filtered, and dried, thereby obtaining 33.7 g (yield 80%) of intermediate B.

$^1$H-NMR (400 MHz, CDCl$_3$) 8.23 (1H), 7.99 (1H), 7.93 (2H), 7.83 (1H), 7.75 (3H), 7.66 (1H), 7.53 (1H), 1.67 (6H)

2) Synthesis of Intermediate C 33.7 g (80.0 mmol) of intermediate B was put in a flask and polyphosphate was added to the flask. Then, the flask was stirred for 2 hours at 130° C. so as to obtain a mixture. The mixture was cooled down to room temperature and distilled water was gradually added to the mixture, thereby obtaining a solid. The obtained solid was filtered and washed using a small amount of methanol, thereby obtaining 26.8 g (yield 83%) of intermediate C.

$^1$H-NMR (400 MHz, CDCl$_3$) 8.84 (1H), 8.12 (1H), 7.78-7.75 (4H), 7.56 (3H), 1.67 (6H)

3) Synthesis of Intermediate E 10 g (24.8 mmol) of intermediate C was put in 250 ml of THF, which was dried under nitrogen atmosphere, so as to obtain a mixture. Then, temperature was lowered to −78° C. and then 50.0 mL (0.5 M) of 2-naphthylmagnesiumbromide was slowly added to the mixture so as to obtain a reaction mixture. Temperature was increased to room temperature and then the reaction mixture was stirred for 3 hours. An ammonium chloride aqueous solution was added to the reaction mixture and then extracted using dichloromethane, thereby obtaining an organic layer. The organic layer was dried using anhydrous magnesium sulfate and a solvent was removed so as to obtain a mixture. The mixture was dissolved using a small amount of ethyl ether, petroleum ether was added to the mixture, and the mixture was stirred for few hours, thereby obtaining a solid compound. The solid compound was vacuum dried and a solid product was obtained. Then, in a nitrogen atmosphere, the solid product was dispersed in 200 ml of acetic acid so as to form a mixture. Then, 41 g (250 mmol) of potassium iodide and 44 g (500 mmol) of sodium hypophosphate hydrate were added to the mixture and then stirred and refluxed for 3 hours so as to form a reaction mixture. After the reaction was completed, an excessive amount of distilled water was added to the reaction mixture so as to form a solid. Then, the solid was filtered, washed using water and methanol, and vacuum dried, thereby obtaining 11.3 g of light-yellow intermediate E (yield 73%).

$^1$H-NMR (400 MHz, CDCl$_3$) 8.10 (1H), 7.95 (1H), 7.91 (2H), 7.70 (2H), 7.73-7.78 (4H), 7.66-7.61 (5H), 7.51 (2H), 7.35 (4H), 7.26 (2H), 1.67 (6H)

4) Synthesis of Intermediate F 6.3 g (10 mmol) of intermediate E was dissolved in 70 ml of THF, which was dried under nitrogen atmosphere, so as to obtain a mixture. Then, 4.8 ml (2.5 M) of butyllithium was added to the mixture at −78° C. so as to form a mixture solution. The mixture solution was stirred for 1 hour at the same temperature and 1.7 ml (15 mmol) of trimethylborate was added to the mixture solution. Temperature was increased to room temperature. After 1 hour, 2 N of aqueous hydrochloric acid was added to the mixture solution and was stirred for 3 hours, thereby obtaining a solid compound. The obtained solid compound was washed using toluene and filtered, thereby obtaining 4.7 g of light-yellow intermediate F (yield 81%).

5) Synthesis of Intermediate G 3.39 g (35.98 mmol) of 2-aminopyridine and 10 g (35.98 mmol) of 2,4'-dibromoacetophenone were dissolved in 150 ml of ethanol so as to form a mixture. Then, the mixture was refluxed for 12 hours. When the mixture was cooled down to room temperature, a white solid was generated and was washed using saturated NaHCO$_3$ solution, thereby obtaining an organic layer. Remaining moisture of the organic layer was removed using anhydrous magnesium sulfate, vacuum dried, and recrystallized (dichloromethane/normal hexane), thereby obtaining 8.02 g of intermediate G having a crystal form of a panel (yield 82%).

6) Synthesis of Compound 2

7.4 g (12.63 mmol) of intermediate F and 2.7 g (11.48 mmol) of intermediate G were put in a mixture solvent of 4.76 g (34.4 mmol) of potassium carbonate aqueous solution and THF so as to form a mixture. Then, 398 mg (3 mol %) of Pd(PPh$_3$)$_4$ was put in the mixture while stirring and refluxed for 6 hours so as to form a mixture solution. The mixture solution was cooled down to room temperature and then a solid compound was generated. The solid compound was filtered while washing using water, ethanol, and THF, thereby obtaining 7.3 g (86%) of compound 2 in the light-yellow powder form.

$^1$H-NMR (400 MHz, CDCl$_3$) 8.10 (1H), 7.94 (2H), 7.91-7.89 (4H), 7.83 (1H), 7.78-7.72 (3H), 7.69-7.65 (5H), 7.54-7.49 (7H), 7.45 (3H), 7.43-7.37 (5H), 6.79 (1H), 1.67 (6H)

Synthesis Example 2

Synthesis of Compound 1

5.9 g (81%) of compound 1 was obtained in the same manner as in Synthesis Example 1, except that phenylmagnesiumbromide was used instead of 2-naphthylmagnesiumbromide when synthesizing intermediate E.

$^1$H-NMR (400 MHz, CDCl$_3$) 8.10 (1H), 8.05-7.89 (4H), 7.71 (2H), 7.63-7.52 (6H), 7.48-7.43 (5H), 7.39-7.32 (6H), 7.23 (2H), 7.10 (1H), 6.79 (1H), 1.67 (6H)

Synthesis Example 3

Synthesis of Compound 3

7.5 g (83%) of compound 3 was obtained in the same manner as in Synthesis Example 1, except that 4-biphenylmagnesiumbromide was used instead of 2-naphthylmagnesiumbromide when synthesizing intermediate E.

$^1$H-NMR (400 MHz, CDCl$_3$) 8.10 (1H), 8.01-7.92 (2H), 7.86 (3H), 7.69 (2H), 7.58-7.52 (13H), 7.48-7.35 (11H), 7.23 (2H), 7.10 (1H), 6.79 (1H), 1.67 (6H)

Synthesis Example 4

Synthesis of Compound 4

7.1 g (79%) of compound 4 was obtained in the same manner as in Synthesis Example 1, except that 2-biphenylmagnesiumbromide was used instead of 2-naphthylmagnesiumbromide when synthesizing intermediate E.

$^1$H-NMR (400 MHz, CDCl$_3$) 8.10 (1H), 8.01-7.92 (2H), 7.86 (3H), 7.75-7.69 (4H), 7.58-7.47 (14H), 7.38-7.32 (8H), 7.23 (2H), 7.08 (1H), 6.79 (1H), 1.67 (6H)

Synthesis Example 5

Synthesis of Compound 5

6.6 g (78%) of compound 5 was obtained in the same manner as in Synthesis Example 1, except that 2-biphenylmagnesiumbromide was used instead of 1-naphthylmagnesiumbromide when synthesizing intermediate E.

$^1$H-NMR (400 MHz, CDCl$_3$) 8.10 (1H), 7.98-7.91 (4H), 7.86 (1H), 7.74-7.61 (8H), 7.58-7.47 (8H), 7.38-7.32 (8H), 7.08 (1H), 6.79 (1H), 1.67 (6H)

Synthesis Example 6

Synthesis of Compound 70

Compound 70 was synthesized according to Reaction Formula 2 below:

<Reaction Formula 2>

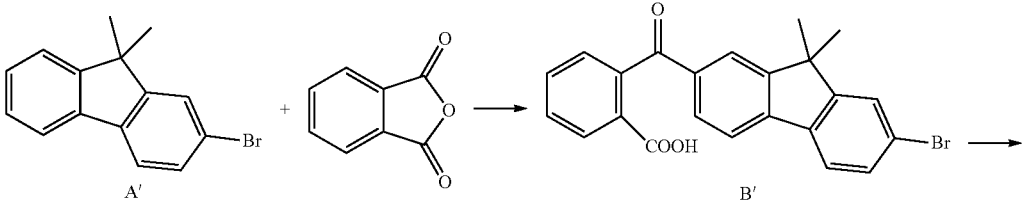

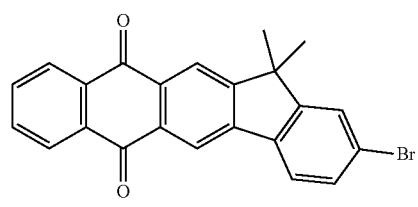
C'
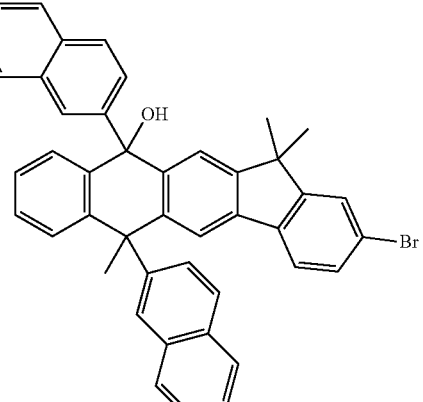
D'
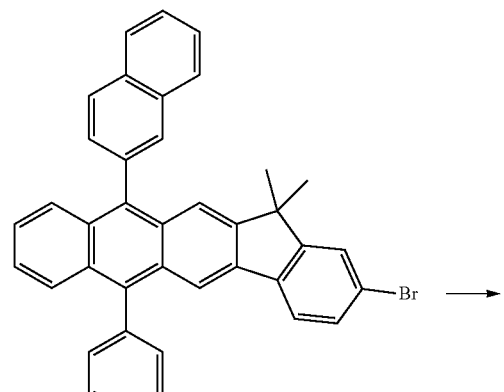
E'
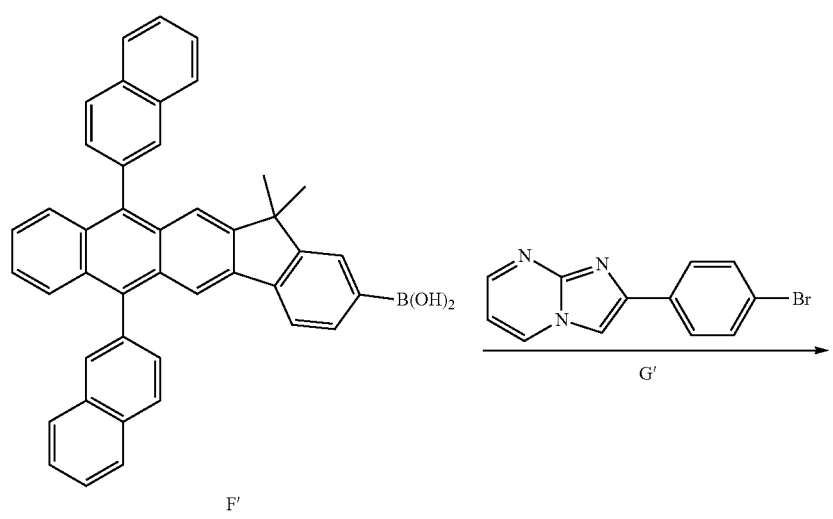
F'  G'

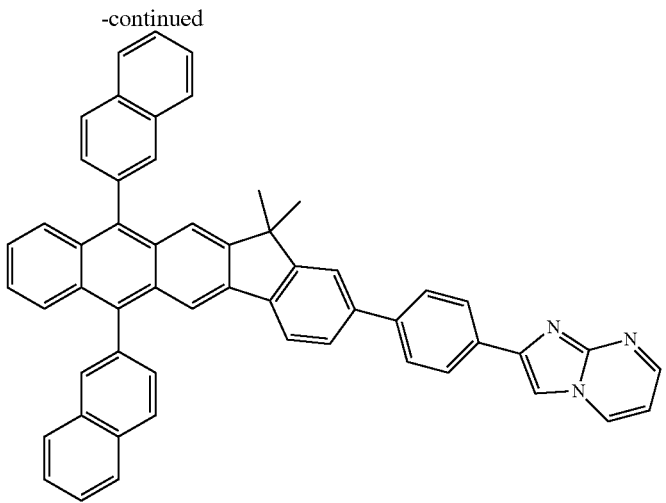

Compound 70

1) Synthesis of Intermediate B'

27.3 g (0.1 mol) of intermediate A' and 16.3 g (0.11 mol) of phthalic anhydride were put in a flask and dichloromethane was added to the flask. 20 g (0.15 mol) of aluminum chloride was gradually added to the flask at 0° C. and then was stirred for 12 hours at room temperature so as to obtain a reaction mixture. After the reaction was completed, distilled water was slowly added to the reaction mixture and was extracted using dichloromethane. Then, a solvent was removed and a solid was obtained. The obtained solid was washed using hexane, filtered, and dried, thereby obtaining 33.7 g (yield 80%) of intermediate B'.

$^1$H-NMR (400 MHz, CDCl$_3$) 8.23 (1H), 7.99 (1H), 7.93 (2H), 7.83 (1H), 7.75 (3H), 7.66 (1H), 7.53 (1H), 1.67 (6H)

2) Synthesis of Intermediate C'

33.7 g (80.0 mmol) of intermediate B' was put in a flask and polyphosphate was added to the flask. Then, the flask was stirred for 2 hours at 130° C. so as to obtain a mixture. The mixture was cooled down to room temperature and distilled water was gradually added to the mixture, thereby obtaining a solid. The obtained solid was filtered and washed using a small amount of methanol, thereby obtaining 26.8 g (yield 83%) of intermediate C'.

$^1$H-NMR (400 MHz, CDCl$_3$) 8.84 (1H), 8.12 (1H), 7.78-7.75 (4H), 7.56 (3H), 1.67 (6H)

3) Synthesis of Intermediate E'

10 g (24.8 mmol) of intermediate C' was put in 250 ml of THF, which was dried under nitrogen atmosphere, so as to obtain a mixture. Then, temperature was lowered to −78° C. and then 50.0 mL (0.5 M) of 2-naphthylmagnesiumbromide was slowly added to the mixture so as to obtain a reaction mixture. Temperature was increased to room temperature and then the reaction mixture was stirred for 3 hours. An ammonium chloride aqueous solution was added to the reaction mixture and then extracted using dichloromethane, thereby obtaining an organic layer. The organic layer was dried using anhydrous magnesium sulfate and a solvent was removed so as to obtain a mixture. The mixture was dissolved using a small amount of ethyl ether, petroleum ether was added to the mixture, and the mixture was stirred for few hoots, thereby obtaining a solid compound. The solid compound was vacuum dried and a solid product was obtained. Then, in a nitrogen atmosphere, the solid product was dispersed in 200 ml of acetic acid so as to form a mixture. Then, 41 g (250 mmol) of potassium iodide and 44 g (500 mmol) of sodium hypophosphate hydrate were added to the mixture and then stirred and refluxed for 3 hours so as to form a reaction mixture. After the reaction was completed, an excessive amount of distilled water was added to the reaction mixture so as to form a solid. Then, the solid was filtered, washed using water and methanol, and vacuum dried, thereby obtaining 11.3 g of light-yellow intermediate E' (yield 73%).

$^1$H-NMR (400 MHz, CDCl$_3$) 8.10 (1H), 7.95 (1H), 7.91 (2H), 7.70 (2H), 7.73-7.78 (4H), 7.66-7.61 (5H), 7.51 (2H), 7.35 (4H), 7.26 (2H), 1.67 (6H)

4) Synthesis of Intermediate F'

6.3 g (10 mmol) of intermediate E' was dissolved in 70 ml of THF, which was dried under nitrogen atmosphere, so as to obtain a mixture. Then, 4.8 ml (2.5 M) of butyllithium was added to the mixture at −78° C. so as to form a mixture solution. The mixture solution was stirred for 1 hour at the same temperature and 1.7 ml (15 mmol) of trimethylborate was added to the mixture solution. Temperature was increased to room temperature. After 1 hour, 2 N of aqueous hydrochloric acid was added to the mixture solution and was stirred for 3 hours, thereby obtaining a solid compound. The obtained solid compound was washed using toluene and filtered, thereby obtaining 4.7 g of light-yellow intermediate F' (yield 81%).

5) Synthesis of Intermediate G'

3.42 g (35.98 mmol) of 2-aminopyridine and 10 g (35.98 mmol) of 2,4'-dibromoacetophenone were dissolved in 150 ml of ethanol so as to form a mixture. Then, the mixture was refluxed for 12 hours. When the mixture was cooled down to room temperature, a white solid was generated and was washed using saturated NaHCO$_3$ solution, thereby obtaining an organic layer. Remaining moisture of the organic layer was removed using anhydrous magnesium sulfate, vacuum dried, and recrystallized (dichloromethane/normal hexane), thereby obtaining 9.86 g of intermediate G' having a crystal form of a panel (yield 87%).

$^1$H-NMR (400 MHz, CDCl$_3$) 8.55 (1H), 8.43 (1H), 7.91 (2H), 7.82 (1H), 7.59 (2H), 6.87 (1H)

6) Synthesis of compound 70

7.5 g (12.63 mmol) of intermediate F' and 2.7 g (11.48 mmol) of intermediate G' were put in a mixture solvent of 4.76 g (34.4 mmol) of potassium carbonate aqueous solution and THF so as to form a mixture. Then, 398 mg (3 mol %) of Pd(PPh$_3$)$_4$ was put in the mixture while stirring and refluxed for 6 hours so as to form a mixture solution. The mixture solution was cooled down to room temperature and then a solid compound was generated. The solid compound was filtered while washing using water, ethanol, and THF, thereby obtaining 6.9 g (82%) of compound 70 in the light-yellow powder form.

$^1$H-NMR (400 MHz, CDCl$_3$) 8.52 (2H), 8.40 (2H), 8.21-7.85 (5H), 7.75-7.66 (8H), 7.54-7.35 (9H), 7.33 (3H), 6.84 (2H), 1.67 (6H)

Synthesis Example 7

Synthesis of Compound 69

5.65 g (77%) of compound 69 was obtained in the same manner as in Synthesis Example 1, except that phenylmagnesiumbromide was used instead of 2-naphthylmagnesiumbromide when synthesizing intermediate E'.

$^1$H-NMR (400 MHz, CDCl$_3$) 8.52 (2H), 8.40 (2H), 8.19-7.85 (5H), 7.73-7.66 (6H), 7.54-7.28 (7H), 7.33 (3H), 6.84 (2H), 1.67 (6H)

Synthesis Example 8

Synthesis of Compound 71

7.27 g (80%) of compound 71 was obtained in the same manner as in Synthesis Example 1, except that 4-biphenylmagnesiumbromide was used instead of 2-naphthylmagnesiumbromide when synthesizing intermediate E'.

$^1$H-NMR (400 MHz, CDCl$_3$) 8.52 (2H), 8.40 (2H), 8.20-7.69 (5H), 7.59-7.45 (16H), 7.38-7.35 (5H), 7.33 (3H), 6.84 (2H), 1.67 (6H)

Synthesis Example 9

Synthesis of Compound 72

7.73 g (85%) of compound 72 was obtained in the same manner as in Synthesis Example 1, except that 2-biphenylmagnesiumbromide was used instead of 2-naphthylmagnesiumbromide when synthesizing intermediate E'.

$^1$H-NMR (400 MHz, CDCl$_3$) 8.52 (2H), 8.40 (2H), 8.20-7.69 (5H), 7.59-7.45 (16H), 7.38-7.35 (5H), 7.33 (3H), 6.84 (2H), 1.67 (6H)

Synthesis Example 10

Synthesis of Compound 73

6.37 g (75%) of compound 73 was obtained in the same manner as in Synthesis Example 1, except that 2-biphenylmagnesiumbromide was used instead of 1-naphthylmagnesiumbromide when synthesizing intermediate E'.

$^1$H-NMR (400 MHz, CDCl$_3$) 8.52 (2H), 8.40 (2H), 7.96-7.78 (5H), 7.68-7.61 (7H), 7.54-7.39 (11H), 7.34 (3H), 6.84 (2H), 1.67 (6H)

Comparative Synthesis Example 1

Synthesis of Compound 201

Compound 201 was manufactured according to Reaction Formula 3 below:

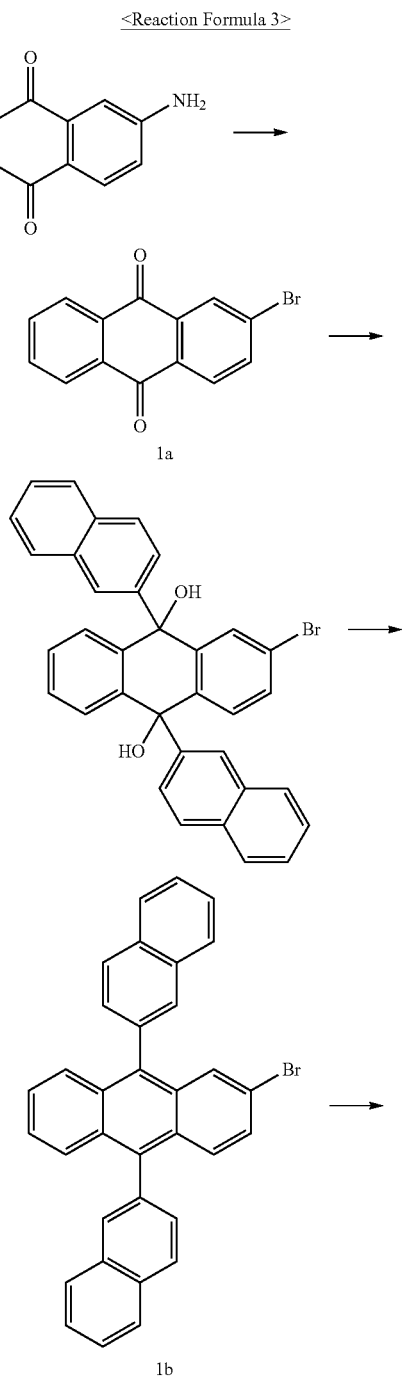

-continued

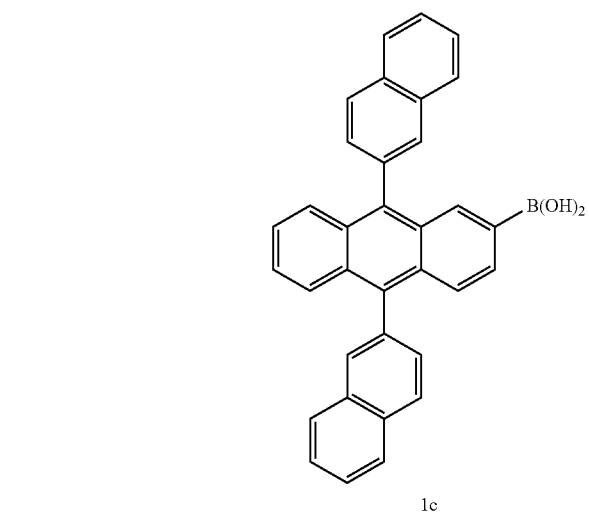
1c

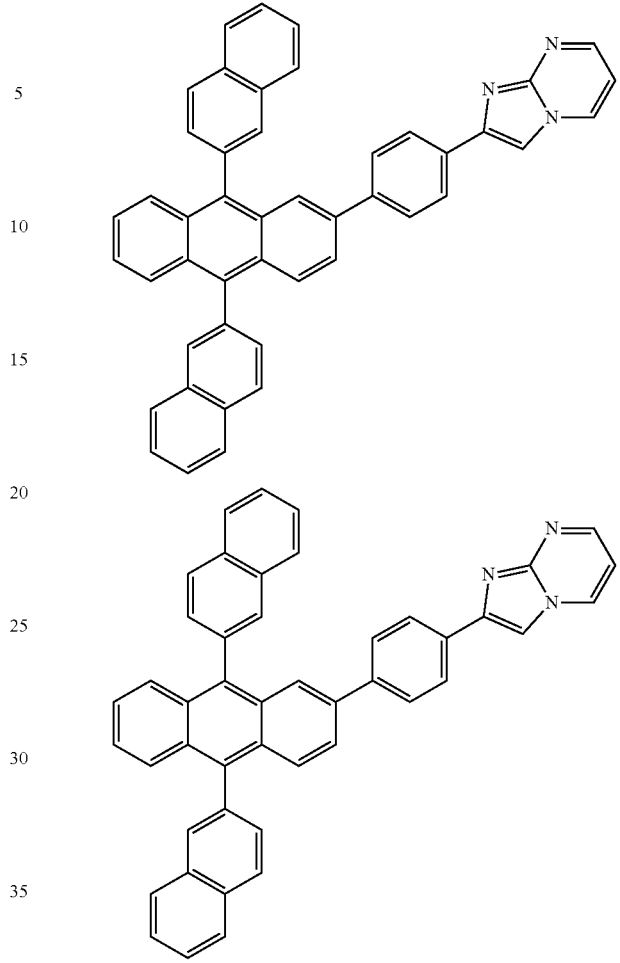
Compound 201

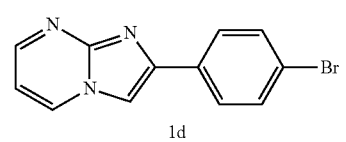
1d

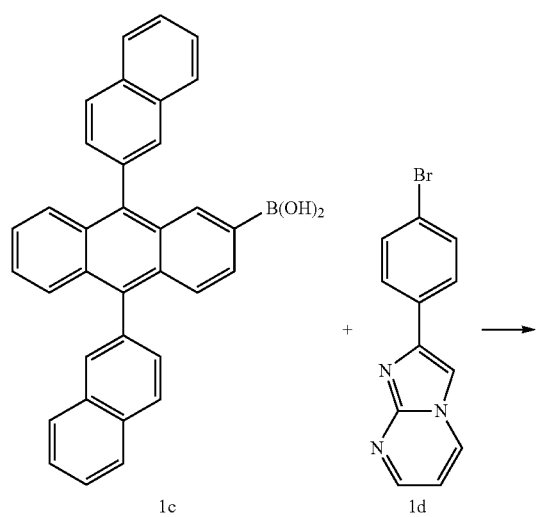
1c    1d

1) Synthesis of Intermediate 1a 10 g (44 mmol) of copper bromide and 8 g (35.8 mmol) of 2-amino-anthraquinon were put in 250 ml of bromic acid so as to form a mixture. The mixture was heated to 65° C. When gas generation was completed, the mixture was cooled down to room temperature so as to form a reaction solution. The reaction solution was added to 1000 ml of 20% aqueous hydrochloric acid and was extracted using dichloromethane, thereby obtaining an organic layer. Remaining moisture of the organic layer was removed using anhydrous magnesium sulfate and vacuum dried, thereby obtaining a product. The product was separated using column chromatography (dichloromethane:normal hexane=4:1), thereby obtaining 7.7 g of intermediate 1a.

2) Synthesis of Intermediate 1b 10 g (34.8 mmol) of intermediate 1a was put in 100 ml of THF, which was dried under nitrogen atmosphere, so as to obtain a mixture. Then, temperature was lowered to −78° C. and then 10 mL (0.5 M) of 2-naphthylmagnesiumbromide was slowly added to the mixture so as to obtain a reaction mixture. Temperature was increased to room temperature and then the reaction mixture was stirred for 3 hours. An ammonium chloride aqueous solution was added to the reaction mixture and then extracted using dichloromethane, thereby obtaining an organic layer. The organic layer was dried using anhydrous magnesium sulfate and a solvent was removed so as to obtain a mixture. The mixture was dissolved using a small amount of ethyl ether, petroleum ether was added to the mixture, and the mixture was stirred for few hours, thereby obtaining a solid compound. The solid compound was filtered and vacuum dried, thereby obtaining 17.6 g of dinaphthyldialcohol.

Then, in a nitrogen atmosphere, 17.6 g (32.4 mmol) of dinaphthyldialcohol was dispersed in 200 ml of acetic acid so as to form a mixture. Then, 53.4 g (330 mmol) of potassium iodide and 58 g (660 mmol) of sodium hypophosphate hydrate were added to the mixture and then stirred and refluxed for 3 hours so as to form a reaction mixture. The mixture was cooled down to room temperature, filtered, and washed using water and methanol, and vacuum dried, thereby obtaining 11.3 g of light-yellow intermediate 1b.

3) Synthesis of Intermediate 1c 5 g (9.81 mmol) of intermediate 1b was dissolved in 70 ml of THF, which was dried under nitrogen atmosphere, so as to obtain a mixture. Then, 4.7 ml (11.8 mmol) of butyllithium was added to the mixture at −78° C. so as to form a mixture solution. The mixture solution was stirred for 1 hour at the same temperature and 2.20 ml (29.4 mmol) of trimethylborate was added to the mixture solution. Temperature was increased to room temperature. After 1 hour, 2 N of aqueous hydrochloric acid was added to the mixture solution and was stirred for 3 hours, thereby obtaining a solid compound. The obtained solid compound was washed using toluene and filtered, thereby obtaining 3.27 g of light-yellow intermediate 1c (yield 70%).

4) Synthesis of Intermediate 1d 3.39 g (35.98 mmol) of 2-aminopyridine and 10 g (35.98 mmol) of 2,4′-dibromoacetophenone were dissolved in 150 ml of ethanol so as to form a mixture. Then, the mixture was refluxed for 12 hours. When the mixture was cooled down to room temperature, a white solid was generated and was filtered while washing using saturated NaHCO$_3$ solution, thereby obtaining an organic layer. Remaining moisture of the organic layer was removed using anhydrous magnesium sulfate, vacuum dried, and recrystallized (dichloromethane/normal hexane), thereby obtaining 8.02 g of intermediate 1d having a crystal form of a panel (yield 82%).

5) Synthesis of Compound 201

1.85 g (3.90 mmol) of intermediate 1c and 1 g (3.90 mmol) of intermediate 1d were put in a mixture solvent of 2.7 g (19.5 mmol) of potassium carbonate aqueous solution and THF so as to form a mixture. Then, 225 mg (0.196 mmol) of Pd(PPh$_3$)$_4$ was put in the mixture while stirring and refluxed for 6 hours so as to form a mixture solution. The mixture solution was cooled down to room temperature and then a solid compound was generated. The solid compound was filtered while washing using water, ethanol, and toluene, thereby obtaining 1.73 g (71%) of compound 201.

$^1$H NMR (400 MHz, CDCl$_3$) 8.51 (1H), 8.40 (1H), 8.12 (1H), 8.06-7.99 (5H), 7.96 (2H), 7.85 (1H), 7.78-7.59 (15H), 7.32 (2H), 6.84 (1H)

Comparative Synthesis Example 2

Synthesis of Compound 202

1.73 g (71%) of compound 202 was obtained in the same manner as in Comparative Synthesis Example 1, except that a compound of intermediate 2d was used instead of 2a compound of intermediate 1d when synthesizing.

1H NMR (400 MHz, CDCl$_3$) 8.13-8.04 (7H), 8.01 (1H), 7.97-7.92 (4H), 7.86-7.82 (2H), 7.75 (2H), 7.71-7.58 (10H), 7.32 (2H), 7.15 (1H), 6.75 (1H)

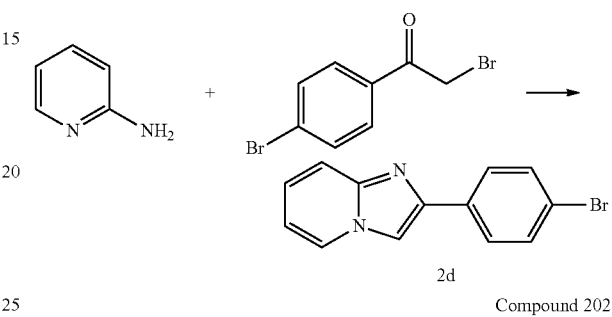

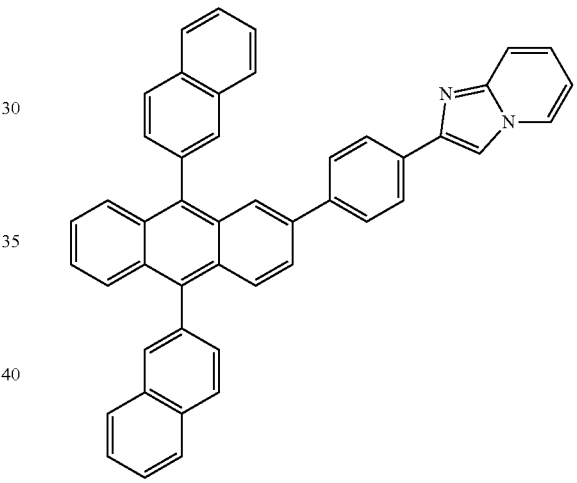

Comparative Synthesis Example 3

Synthesis of Compound 203

Intermediate E-1 was synthesized in the same manner as in Synthesis Example 1, except that a phenyl group was used instead of a naphtyl group when synthesizing intermediate E. 2.05 g (3.90 mmol) of intermediate E-1 and 1.23 g (3.90 mmol) of intermediate H were put in a mixture solvent of 2.7 g (19.5 mmol) of potassium carbonate aqueous solution and toluene so as to form a mixture. Then, 225 mg (0.196 mmol) of Pd(PPh$_3$)$_4$ was put in the mixture while stirring and refluxed for 6 hours so as to form a mixture solution. The mixture solution was cooled down to room temperature and then a solid compound was generated. The solid compound was filtered while washing using water, ethanol, and toluene, thereby obtaining 1.74 g (70%) of compound 203.

$^1$H-NMR (400 MHz, CDCl$_3$) 8.52 (1H), 8.27 (1H), 8.10 (1H), 7.83 (2H), 7.74 (1H), 7.68 (4H), 7.59-7.42 (16H), 7.22 (2H), 1.67 (6H)

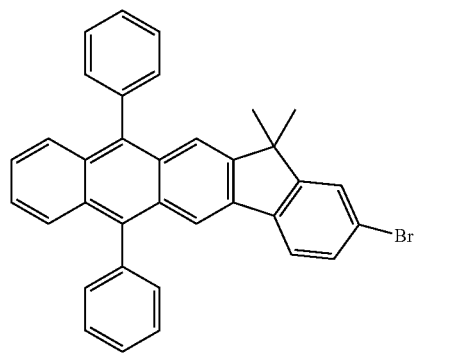

E-1

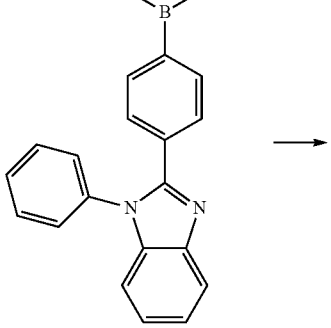

H

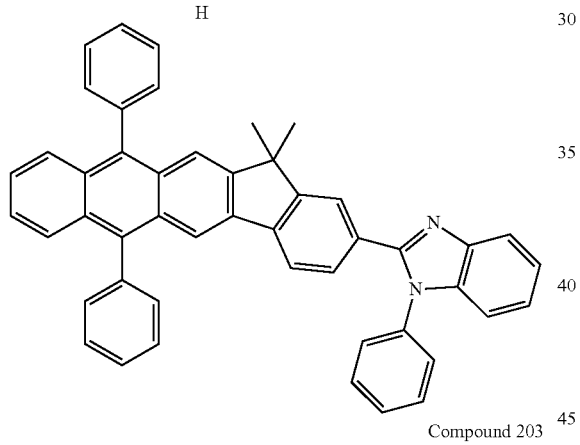

Compound 203

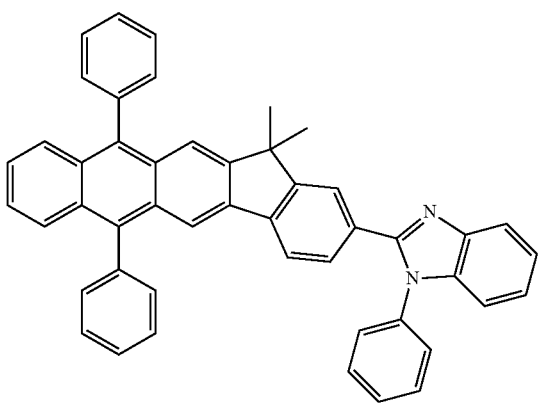

Example 1

As an anode, 15 Ω/cm² (1200 Å) of an ITO glass substrate from Corning Co., Ltd. was cut into 50 mm×50 mm×0.7 mm and was ultrasonic washed for 5 minutes respectively using isopropyl alcohol and purified water. Then, ultraviolet rays were irradiated to the washed ITO glass substrate for 15 minutes and washed by being exposed to ozone. Then, the ITO glass substrate was deposited in a vacuum deposition device. m-MTDATA was vacuum deposited on the ITO glass substrate so as to form a hole injection layer having a thickness of 600 Å. Then, NPB was vacuum deposited on the hole injection layer, thereby forming a hole transport layer having a thickness of 300 Å.

98% of $Alq_3$, as a green emission host, and 2% of C545T, as a green dopant, were used to form an emission layer having a thickness of 300 Å. Compound 1 was vacuum deposited on the emission layer so as to form an electron transport layer having a thickness of 300 Å. LiF was vacuum deposited on the electron transport layer so as to form an electron injection layer having a thickness of 10 Å and then Al was vacuum deposited on the electron injection layer so as to form a cathode having a thickness of 3000 Å. Therefore, an organic light-emitting device was completely manufactured.

Example 2

An organic light-emitting device was completely manufactured in the same manner as in Example 1, except that compound 2 was used instead of compound 1 when forming the electron transport layer.

Example 3

An organic light-emitting device was completely manufactured in the same manner as in Example 1, except that compound 3 was used instead of compound 1 when forming the electron transport layer.

Example 4

An organic light-emitting device was completely manufactured in the same manner as in Example 1, except that compound 4 was used instead of compound 1 when forming the electron transport layer.

Example 5

An organic light-emitting device was completely manufactured in the same manner as in Example 1, except that compound 5 was used instead of compound 1 when forming the electron transport layer.

Example 6

An organic light-emitting device was completely manufactured in the same manner as in Example 1, except that compound 69 was used instead of compound 1 when forming the electron transport layer.

Example 7

An organic light-emitting device was completely manufactured in the same manner as in Example 1, except that compound 70 was used instead of compound 1 when forming the electron transport layer.

Example 8

An organic light-emitting device was completely manufactured in the same manner as in Example 1, except that compound 71 was used instead of compound 1 when forming the electron transport layer.

Example 9

An organic light-emitting device was completely manufactured in the same manner as in Example 1, except that compound 72 was used instead of compound 1 when forming the electron transport layer.

Example 10

An organic light-emitting device was completely manufactured in the same manner as in Example 1, except that compound 73 was used instead of compound 1 when forming the electron transport layer.

Comparative Example 1

An organic light-emitting device was completely manufactured in the same manner as in Example 1, except that Alq$_3$ (aluminum tris(8-hydroxyquinoline)) was used instead of compound 1 when forming the electron transport layer.

Comparative Example 2

An organic light-emitting device was completely manufactured in the same manner as in Example 1, except that compound 201 was used instead of compound 1 when forming the electron transport layer.

Comparative Example 3

An organic light-emitting device was completely manufactured in the same manner as in Example 1, except that compound 202 was used instead of compound 1 when forming the electron transport layer.

Comparative Example 4

An organic light-emitting device was completely manufactured in the same manner as in Example 1, except that compound 203 was used instead of compound 1 when forming the electron transport layer.

Evaluation Example

The organic light-emitting devices of Examples 1 through 10 and the organic light-emitting devices of Comparative Examples 1 through 4 were evaluated in terms of current density, driving voltage, efficiency, and color coordinates using PR650 (Spectroscan) Source Measurement Unit (PhotoResearch Co. LTD.). The results are shown in Table 1 below.

TABLE 1

| | Electron transport layer | Driving voltage (V) | Current density (mA/cm$^2$) | Emission Efficiency (cd/A) | Color Coordiates |
|---|---|---|---|---|---|
| Example 1 | Compound 1 | 6.5 | 50 | 15.2 | (0.309, 0.641) |
| Example 2 | Compound 2 | 6.5 | 50 | 18.8 | (0.309, 0.641) |
| Example 3 | Compound 3 | 6.2 | 50 | 16.3 | (0.309, 0.641) |
| Example 4 | Compound 4 | 6.4 | 50 | 14.9 | (0.309, 0.643) |
| Example 5 | Compound 5 | 6.1 | 50 | 16.8 | (0.309, 0.642) |
| Example 6 | Compound 69 | 6.3 | 50 | 16.4 | (0.309, 0.642) |
| Example 7 | Compound 70 | 6.3 | 50 | 15.1 | (0.309, 0.641) |
| Example 8 | Compound 71 | 6.4 | 50 | 15.9 | (0.310, 0.643) |
| Example 9 | Compound 72 | 6.3 | 50 | 16.5 | (0.309, 0.641) |
| Example 10 | Compound 73 | 6.5 | 50 | 14.7 | (0.310, 0.642) |
| Comparative Example 1 | Alq$_3$ | 7.5 | 50 | 11.9 | (0.309, 0.641) |
| Comparative Example 2 | Compound 201 | 6.5 | 50 | 13.2 | (0.310, 0.642) |
| Comparative Example 3 | Compound 202 | 6.7 | 50 | 12.3 | (0.310, 0.642) |
| Comparative Example 4 | Compound 203 | 7.4 | 50 | 13.7 | (0.310, 0.641) |

According to Table 1, the organic light-emitting devices of Examples 1 through 10 have excellent performance, for example, low driving voltages and high emission efficiencies, compared with the organic light-emitting devices of Comparative Examples 1 through 4.

The organic light-emitting device including the condensed-cyclic compound represented by Formula 1 has low driving voltage and high emission efficiency and thus a flat panel display apparatus has excellent performance.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A condensed-cyclic compound represented by Formula 1 below:

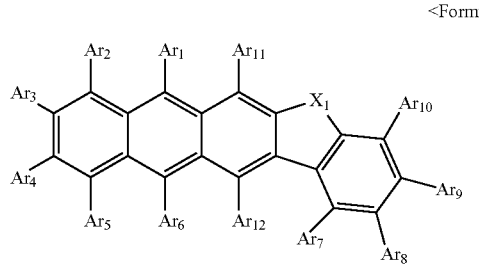

<Formula 1> wherein $X_1$ is $CR_1R_2$, $NR_3$, or O;

$Ar_1$ through $Ar_8$ and $Ar_{10}$ through $Ar_{12}$ are each independently one selected from the group consisting of a hydrogen atom, deuterium, a halogen atom, a hydroxyl group, a cyano group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ aryloxy group, a substituted or unsubstituted $C_5$-$C_{30}$ arylthio group, a substituted or unsubstituted $C_2$-$C_{30}$ heterocyclic group, a group represented by $N(Q_1)(Q_2)$, and a group represented by $Si(Q_3)(Q_4)(Q_5)$, wherein $Q_1$ through $Q_5$ are each independently one selected from the group consisting of a hydrogen atom, deuterium, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$) alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ aryloxy group, a substituted or unsubstituted $C_5$-$C_{30}$ arylthio group, and a substituted or unsubstituted $C_2$-$C_{30}$ heterocyclic group, $Ar_9$ is a group represented by Formula 2 below;

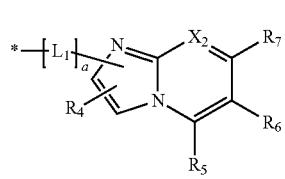

<Formula 2>

$L_1$ is a substituted or unsubstituted $C_1$-$C_{30}$ alkylene group, a substituted or unsubstituted $C_5$-$C_{30}$ arylene group, or a substituted or unsubstituted divalent $C_2$-$C_{30}$ heterocyclic group;

$X_2$ is N;

a is an integer from 0 to 5; and $R_1$ through $R_8$ are each independently one selected from the group consisting of a hydrogen atom, deuterium, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ aryloxy group, a substituted or unsubstituted $C_5$-$C_{30}$ arylthio group, and a substituted or unsubstituted $C_2$-$C_{30}$ heterocyclic group, wherein at least two of $R_4$ through $R_8$ that are adjacent to each other may be combined with each other to form a saturated or unsaturated ring and plural groups in $R_4$ through $R_8$ may be the same as each other or different from each other.

2. The condensed-cyclic compound of claim 1, wherein $X_1$ is $CR_1R_2$ and $R_1$ and $R_2$ are as defined in claim 1.

3. The condensed-cyclic compound of claim 1, wherein $R_1$ through $R_3$ are each independently one selected from the group consisting of a hydrogen atom, deuterium, a halogen atom, a hydroxyl group, a cyano group, an amino group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted naphtyl group, a substituted or unsubstituted fluorenyl group, a substituted or unsubstituted spiro-fluorenyl group, a substituted or unsubstituted anthryl group, a substituted or unsubstituted pyrazolyl group, a substituted or unsubstituted pyridinyl group, a substituted or unsubstituted pyrazinyl group, a substituted or unsubstituted pyrimidinyl group, and a substituted or unsubstituted pyridazinyl group.

4. The condensed-cyclic compound of claim 1, wherein $Ar_2$, $Ar_5$, $Ar_7$, $Ar_8$, $Ar_{10}$, $Ar_{11}$, and $Ar_{12}$ are all hydrogen atoms, and $Ar_1$, $Ar_3$, $Ar_4$ and $Ar_6$ are each independently one selected from the group consisting of deuterium, a halogen atom, a hydroxyl group, a cyano group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ aryloxy group, a substituted or unsubstituted $C_5$-$C_{30}$ arylthio group, a substituted or unsubstituted $C_2$-$C_{30}$ heterocyclic group, a group represented by N(Q₁)(Q₂), and a group represented by Si(Q₃)(Q₄)(Q₅), wherein Ar₉ is a group represented by Formula 2 of claim 1 and Q₁ through Q₅ are as defined in claim 1.

5. The condensed-cyclic compound of claim wherein Ar₁ through Ar₈ and Ar₁₀ through Ar₁₂ are each independently one selected from the group consisting of a hydrogen atom, deuterium, a halogen atom, a hydroxyl group, a cyano group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted pentalenyl group, a substituted or unsubstituted indenyl group, a substituted or unsubstituted naphtyl group, a substituted or unsubstituted azulenyl group, a substituted or unsubstituted heptalenyl group, a substituted or unsubstituted indacenyl group, a substituted or unsubstituted acenaphtyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzooxazolyl group, a substituted or unsubstituted benzoimidazolyl group, a substituted or unsubstituted furanyl, a substituted or unsubstituted benzofuranyl group, a substituted or unsubstituted thiophenyl group, a substituted or unsubstituted benzothiophenyl group, a substituted or unsubstituted thiazolyl group, a substituted or unsubstituted isothiazolyl group, a substituted or unsubstituted benzothiazolyl group, a substituted or unsubstituted isoxazolyl group, a substituted or unsubstituted oxazolyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted benzooxazolyl group, a substituted or unsubstituted dibenzofuranyl group, a substituted or unsubstituted dibenzothiophenyl group, a group represented by N(Q₁)(Q₂), and a group represented by Si(Q₃)(Q₄)(Q₅) where Q₁ through Q₅ are as defined in claim 1.

6. The condensed-cyclic compound of claim 1, wherein L₁ in Formula 2 is one selected from the group consisting of a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphtylene group, a substituted or unsubstituted fluorenylene group, a substituted or unsubstituted spiro-fluorenyl group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, and a substituted or unsubstituted hexylenylene group.

7. The condensed-cyclic compound of claim 1, wherein "a" in Formula 2 is 1 or 2.

8. The condensed-cyclic compound of claim 1, wherein R₄ through R₈ in Formula 2 above are each independently one selected from the group consisting of a hydrogen atom, deuterium, a halogen atom, a hydroxyl group, a cyano group, an amino group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted naphtyl group, a substituted or unsubstituted fluorenyl group, a substituted or unsubstituted spiro-fluorenyl group, a substituted or unsubstituted anthryl group, a substituted or unsubstituted pyrazolyl group, a substituted or unsubstituted pyridinyl group, a substituted or unsubstituted pyrazinyl group, a substituted or unsubstituted pyrimidinyl group, and a substituted or unsubstituted pyridazinyl group.

9. The condensed-cyclic compound of claim 1, wherein the group represented by Formula 2 is one of the groups represented by Formulas 2I through 2N below:

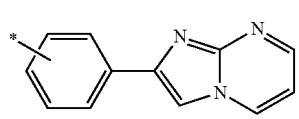

<Formula 2I>

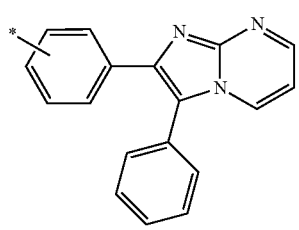

<Formula 2J>

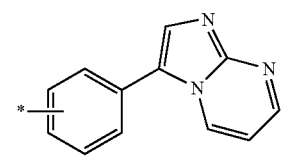

<Formula 2K>

<Formula 2L>
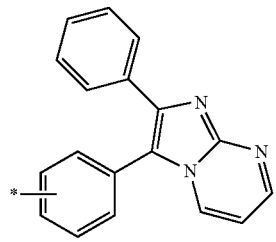
<Formula 2M>
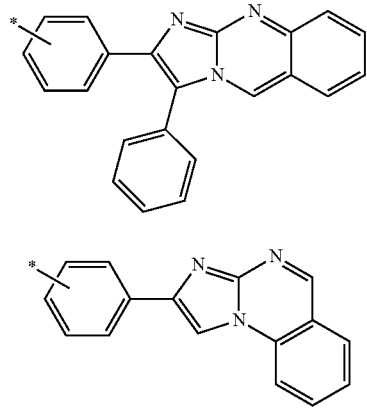
<Formula 2N>
wherein "*" represents a chemical bond.
wherein "*" represents a chemical bond.
10. The condensed-cyclic compound of claim 1, wherein the condensed-cyclic compound represented by Formula 1 is one of compounds represented by Compounds 69, 70, 71, 72, or 73 below:
<Compound 69>
<Compound 70>
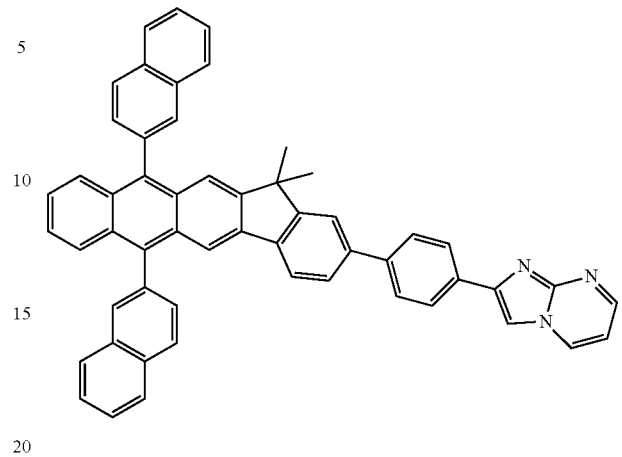
<Compound 71>
<Compound 72>
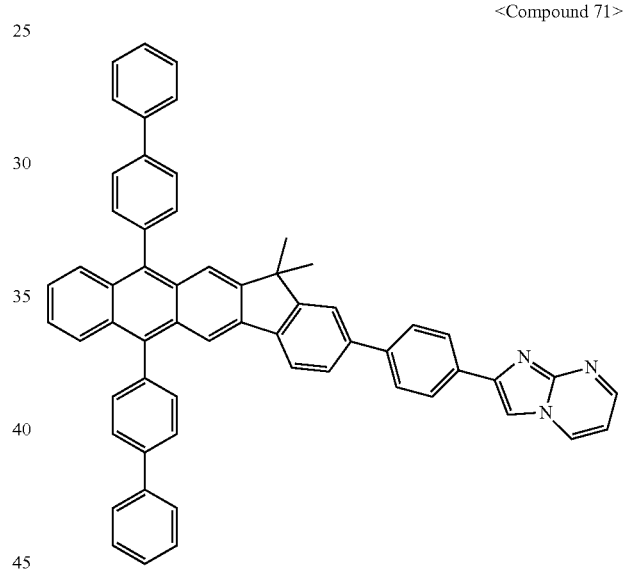
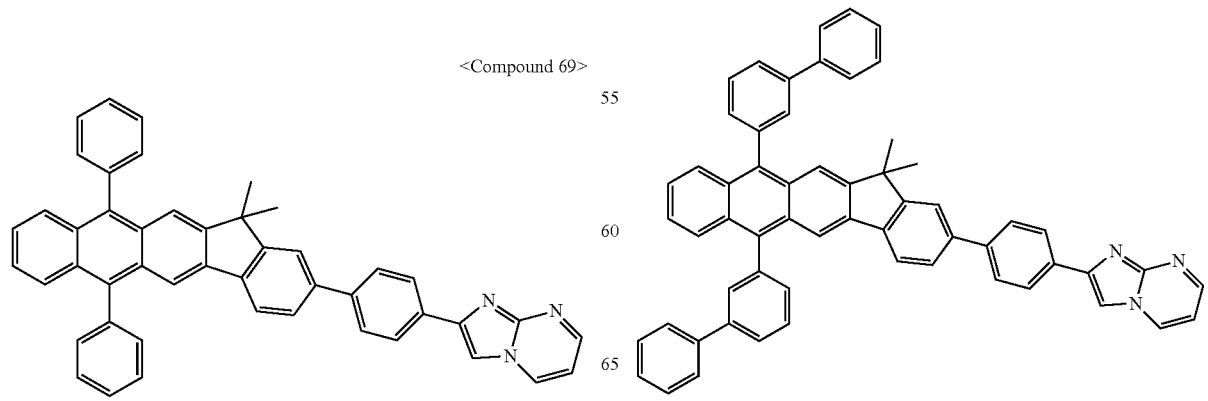

<Compound 73>

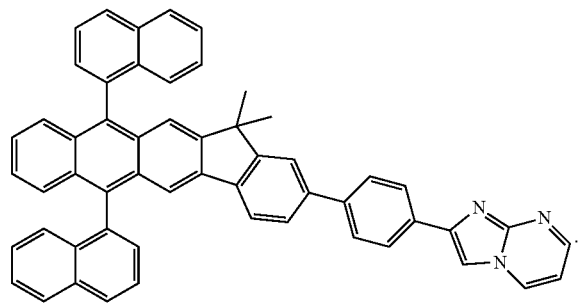

11. An organic light-emitting device comprising:
a first electrode;
a second electrode; and
an organic light-emitting device comprising at least one organic layer interposed between the first electrode and the second electrode,
wherein the at least one organic layer comprises the condensed-cyclic compound of claim 1.

12. The organic light-emitting device of claim 11, wherein the organic layer comprises an electron injection layer, an electron transport layer, or a single layer simultaneously having an electron injection function and an electron transport function.

13. The organic light-emitting device of claim 11, further comprising at least one emission layer interposed between the first electrode and the second electrode, wherein the at least one organic layer is the electron transport layer and the emission layer comprises a fluorescent or phosphorescent host.

14. The organic light-emitting device of claim 11, wherein the at least one organic layer is an emission layer.

15. The organic light-emitting device of claim 11, further comprising between the first electrode and the second electrode at least one selected from the group consisting of a hole injection layer, a hole transport layer, an electron blocking layer, a hole blocking layer, an electron transport layer, and an electron injection layer.

16. A flat panel display apparatus comprising a transistor comprising a source electrode, a drain electrode, a gate, and an active layer, and the organic light-emitting device of claim 11, wherein a first electrode of the organic light-emitting device is electrically connected to the source electrode or the drain electrode.

* * * * *